(12) United States Patent
Jadhav et al.

(10) Patent No.: US 8,486,943 B2
(45) Date of Patent: Jul. 16, 2013

(54) TETRAHYDROCYCLOPENTA[B]INDOLE ANDROGEN RECEPTOR MODULATORS

(75) Inventors: Prabhakar Kondaji Jadhav, Zionsville, IN (US); Venkatesh Krishnan, Fishers, IN (US); Euibong Jemes Kim, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 36 days.

(21) Appl. No.: 12/989,959

(22) PCT Filed: May 14, 2009

(86) PCT No.: PCT/US2009/043875
§ 371 (c)(1),
(2), (4) Date: Oct. 28, 2010

(87) PCT Pub. No.: WO2009/140448
PCT Pub. Date: Nov. 19, 2009

(65) Prior Publication Data
US 2011/0039855 A1    Feb. 17, 2011

Related U.S. Application Data

(60) Provisional application No. 61/053,722, filed on May 16, 2008.

(51) Int. Cl.
*A61K 31/403*    (2006.01)
*C07D 209/60*    (2006.01)

(52) U.S. Cl.
USPC ............................. 514/243; 514/411; 548/427

(58) Field of Classification Search
USPC .......................................... 514/411; 548/427
See application file for complete search history.

(56) References Cited

U.S. PATENT DOCUMENTS

| | | | |
|---|---|---|---|
| 4,988,820 A | 1/1991 | Boshagen et al. |
| 5,204,374 A | 4/1993 | Muller et al. |
| 5,223,517 A | 6/1993 | Muller et al. |
| 5,272,161 A | 12/1993 | Niewohner et al. |
| 5,374,647 A | 12/1994 | Bohagen et al. |
| 7,122,570 B2 | 10/2006 | Koppitz et al. |
| 2005/0171143 A1 | 8/2005 | Tanimoto et al. |
| 2006/0074124 A1 | 4/2006 | Napper et al. |

FOREIGN PATENT DOCUMENTS

| | | |
|---|---|---|
| WO | 03014082 | 2/2003 |
| WO | 2005056527 | 6/2005 |
| WO | 2005092854 | 10/2005 |
| WO | 2006065480 | 6/2006 |
| WO | 2006089053 | 8/2006 |
| WO | 2007002181 | 1/2007 |
| WO | 2007047604 | 4/2007 |
| WO | 2008019825 | 2/2008 |
| WO | 2008063867 | 5/2008 |
| WO | WO2008063867 | * 5/2008 |
| WO | WO 2008063867 A2 | * 5/2008 |

OTHER PUBLICATIONS

Patani, G., et al. Bioisosterism: A Rational Approach in Drug Design. Chemical Reviews 96, 3147-3176. 1996.*
Rosen, R.C., et al. Overview of Phosphodiesterase 5 Inhibition in Erectile Dysfunction. American Journal of Cardiology 92, (Supplemental 9M-18M). 2003.*
Brown, "Nonsteroidal Selective Androgen Receptors Modulators (SARMs): Designer Androgens with Flexible Structures Provide Clinical Promise," Endocrinology, vol. 145, No. 12, pp. 5417-5419 (2004).
Cadillia, et al, "Selective Androgen Receptor Modulators in Drug Discovery: Medicinal Chemistry and Therapeutic Potential," Current Top. Med. Chem., vol. 6, No. 3, pp. 245-270 (2006).
Segal, et al., "Therapeutic Potential of the SARMs: Revisiting the Androgen Receptor for Drug Discovery," Exp. Opinion and Invest. Drugs, vol. 15, No. 4, pp. 377-387 (2006).
Golob, et al., "Antiestrogenic Activities of 3,8-Dihydroxy-6,11-dihydrobenzo[a]carbazoles with Sulfur-Containing Side Chains," Arch. Pharm. Pharm. Med. Chem., vol. 33, No. 9, pp. 305-311 (2000).
Written Opinion of PCT/US2007/083745, Dated Jun. 10, 2008.
Demand of PCT1US2007/083745, Dated Jun. 10, 2008.
Reply to Written Opinion of PCT/US2007/083745, Written by Applicants on Aug. 28, 2008.
IPRP for PCT/US2007/083745, Dated Mar. 25, 2009.
Rejection for U.S. Appl. No. 11/917398, Received by Applicants on Jun. 10, 2010.

* cited by examiner

*Primary Examiner* — Paul Zarek
*Assistant Examiner* — George W Kosturko
(74) *Attorney, Agent, or Firm* — Elizabeth A. Dingess-Hammond; Alexander Wilson

(57) ABSTRACT

The present invention provides a compound of the Formula (I), or a pharmaceutically acceptable salt thereof; pharmaceutical compositions comprising a compound of Formula (I) in combination with a suitable carrier, diluent, or excipient; and methods for treating or preventing physiological disorders, particularly reduced bone mass, osteoporosis, osteopenia, reduced muscle mass or strength, or erectile dysfunction comprising administering a compound of Formula (I), or a pharmaceutically acceptable salt thereof.

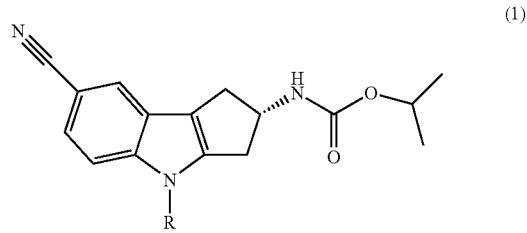

(1)

13 Claims, No Drawings

TETRAHYDROCYCLOPENTA[B]INDOLE ANDROGEN RECEPTOR MODULATORS

This application is the U.S. National Stage filing of PCT Application No. PCT/US2009/043875, filed May 14, 2009, which claims the benefit under 35 USC 119(e) of U.S. Provisional Application No. 61/053,722, filed May 16, 2008.

Endogenous steroidal androgens (e.g. testosterone and 5α-dihydrotestosterone (DHT) exert profound influences on a multitude of physiological functions. Clinically, androgen therapy has been used in the treatment of hypogonadism in men. Significantly, androgen replacement therapy in hypogonadal men has also been shown to decrease bone resorption and increase bone mass. Other indications for which androgens have been used clinically include osteoporosis, and muscle wasting diseases. In addition, androgen replacement therapy has been used recently in aging men and for the regulation of male fertility. In females, androgen therapy has been used clinically for the treatment of sexual dysfunction or diminished libido.

However, androgen therapy has limitations. For example, unwanted side effects of steroidal androgen therapy include growth stimulation of the prostate and seminal vesicles. In addition, stimulation of prostate tumors and elevations in prostate specific antigen (PSA) (an indication of increased prostate cancer risk) have been associated with androgen use. Furthermore, preparations of steroidal androgens have been found to suffer from rapid degradation in the liver leading to poor oral bioavailability and short duration of activity following parenteral administration, variations in plasma levels, hepatotoxicity, or cross reactivity with other steroid hormone receptors (e.g. the glucocorticoid receptor (GR), the mineralocorticoid receptor (MR), and the progesterone receptor (PR)). Furthermore, in females, the use of steroidal androgens may lead to hirsutism or virilization.

Thus, there remains a need in the art for alternatives to steroidal androgen therapy. Preferably, such alternatives possess the beneficial pharmacological properties of steroidal androgens, but with a reduced likelihood or incidence of the typical limitations associated with steroidal androgen therapy. It is therefore an object of the present invention to provide nonsteroidal AR ligands which possess androgen agonist activity. More particularly, it is an object to provide nonsteroidal androgen agonists which bind to AR with greater affinity relative to the other steroid hormone receptors. Even more particularly, it is an object to provide tissue selective androgen receptor modulators (SARMs) which display androgen agonist activity in muscle or bone, but only partial agonist, partial antagonist or antagonist activity in androgenic tissues such as the prostate or seminal vesicle.

The following provide examples of the current state of the art: Cadilla et al., *Curr. Top. Med. Chem* (2006); 6(3): 245-270, provides a review of androgen receptor modulators; Segal et al., *Expert Opin. Investig. Drugs* (2006); 15(4); 377-387, provides a review of androgen receptor modulators; Co-pending international patent application PCT/US07/83745 discloses tetrahydrocyclopenta[b]indole compounds as androgen receptor modulators; and Published international patent application WO 2007/83745 discloses tetrahydrocarbazoles as androgen receptor modulators.

The present invention is directed to certain tetrahydrocyclopenta[b]indole compounds, as defined by Formula (I) below, which have particular profiles of activity in in vitro and in vivo testing which suggest they are useful in the treatment of disorders responsive to steroidal androgen therapy. Accordingly, the present invention provides a compound of Formula (I):

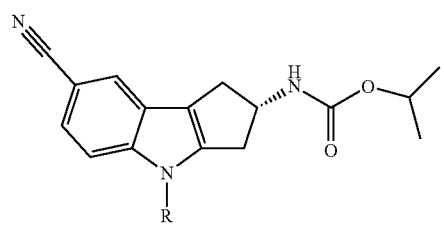

Formula (I)

wherein,
R represents a substitutent selected from the group consisting of

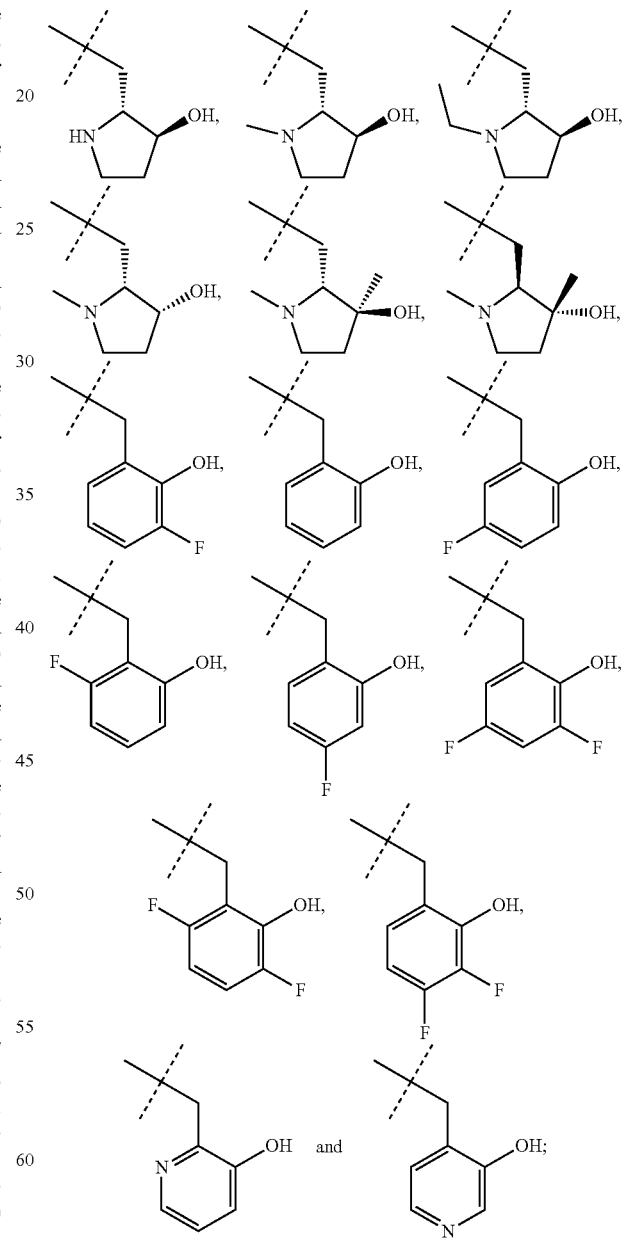

or a pharmaceutically acceptable salt thereof.

In another embodiment, the present invention provides a method of treating or preventing hypogonadism, reduced bone mass or density, osteoporosis, osteopenia, reduced muscle mass or strength, male or female sexual dysfunction, erectile dysfunction, or reduced libido comprising administering to a patient in need thereof an effective amount of a compound of Formula (I), or a pharmaceutically acceptable salt thereof. As a particular aspect, the present invention provides a method for treating or preventing reduced bone mass or density, osteoporosis, osteopenia, reduced muscle mass or strength, or erectile dysfunction. As a more particular aspect, the present invention provides a method for treating or preventing reduced bone mass or density, osteoporosis, osteopenia, reduced muscle mass or strength induced by immobilization, disuse or trauma, or erectile dysfunction.

Further, the present invention provides a compound of Formula (I), or a pharmaceutically acceptable salt thereof, for use in the treatment or prevention of hypogonadism, reduced bone mass or density, osteoporosis, osteopenia, reduced muscle mass or strength, male or female sexual dysfunction, erectile dysfunction, or reduced libido. More particularly, the invention provides a compound of Formula (I), or a pharmaceutically acceptable salt thereof, for use in the treatment or prevention of reduced bone mass or density, osteoporosis, osteopenia, reduced muscle mass or strength, or erectile dysfunction. Even more particularly, the present invention provides a compound of Formula (I), or a pharmaceutically acceptable salt thereof, for use in the treatment or prevention of reduced bone mass or density, osteoporosis, osteopenia, reduced muscle mass or strength induced by immobilization, disuse or trauma, or erectile dysfunction. In addition, the present invention provides a compound of Formula (I), or a pharmaceutically acceptable salt thereof, for use in therapy.

In another embodiment, the present invention provides the use of a compound of Formula (I), or a pharmaceutically acceptable salt thereof for the manufacture of a medicament for the treatment or prevention of hypogonadism, reduced bone mass or density, osteoporosis, osteopenia, reduced muscle mass or strength, male or female sexual dysfunction, erectile dysfunction, or reduced libido. More particularly, the present invention provides the use of a compound of Formula (I) for the manufacture of a medicament for the treatment or prevention of reduced bone mass or density, osteoporosis, osteopenia, reduced muscle mass or strength, or erectile dysfunction. Even more particularly, the present invention provides the use of a compound of Formula (I) for the manufacture of a medicament for the treatment or prevention of reduced bone mass or density, osteoporosis, osteopenia, reduced muscle mass or strength induced by immobilization, disuse or trauma, or erectile dysfunction.

In addition, the present invention provides a pharmaceutical composition comprising a compound of Formula (I), or a pharmaceutically acceptable salt thereof, in combination with one of more pharmaceutically acceptable carriers, diluents, or excipients. More particularly, the present invention provides a pharmaceutical composition for the treatment of reduced bone mass or density, osteoporosis, osteopenia, reduced muscle mass or strength, or erectile dysfunction comprising a compound of Formula (I), or a pharmaceutically acceptable salt thereof, in combination with one or more pharmaceutically acceptable carriers, diluents or excipients. Even more particularly, the present invention provides a pharmaceutical composition for the treatment of reduced bone mass or density, osteoporosis, osteopenia, reduced muscle mass or strength induced by immobilization, disuse or trauma, or erectile dysfunction.

The present invention also encompasses novel intermediates and processes useful for the synthesis of a compound of Formula (I).

The present invention also relates to pharmaceutically acceptable salts of the compound of Formula (I). Examples of pharmaceutically acceptable salts and methods for their preparation are well within the knowledge of those skilled in the art. In addition, the present invention also relates to solvates of the compound of Formula (I) or the pharmaceutically acceptable salts of compounds of Formula (I). As such, when used herein the term "Formula (I)", or any particular compound of Formula (I), includes within its meaning any solvate of the compound.

The compounds of Formula (I) may have one or more chiral centers and, therefore, may exist in particular stereoisomeric configurations. The terms "R" and "S" are used herein as commonly used in organic chemistry to denote specific configurations of a chiral center. The terms "(±)" or "RS" refer to a configuration of a chiral center comprising a racemate. A partial list of priorities and a discussion of stereochemistry is contained in "Nomenclature of Organic Compounds: Principles and Practice", (J. H. Fletcher, et al., eds., 1974). X-ray analysis and correlation with chiral-HPLC retention time.

The specific stereoisomers and enantiomers of compounds of Formula I can be prepared by one of ordinary skill in the art utilizing well known techniques and processes, such as those disclosed by Eliel and Wilen, "Stereochemistry of Organic Compounds", John Wiley & Sons, Inc., 1994, Chapter 7; Separation of Stereoisomers, Resolution, Racemization; and by Collet and Wilen, "Enantiomers, Racemates, and Resolutions", John Wiley & Sons, Inc., 1981. For example, specific stereoisomers and enantiomers can be prepared by stereospecific syntheses using enantiomerically and geometrically pure, or enantiomerically or geometrically enriched starting materials. In addition, the specific stereoisomers and enantiomers can be resolved and recovered by techniques such as chromatography on chiral stationary phases, enzymatic resolution, fractional recrystallization of addition salts, as well as those techniques provided in the Schemes and Examples herein.

The designation "―■" refers to a bond that protrudes forward out of the plane of the page.

The designation "⋯⋯⋯⋯" refers to a bond that protrudes backward out of the plane of the page.

The designation "⟋⟋⟋" refers to a bond that exists as a mixture of bonds that protrude both forward and backward out of the plane of the page.

As used herein the term "patient" refers to a human or nonhuman mammal such as a dog, cat, cow, monkey, horse, or sheep. More particularly, the term "patient" refers to a human. The term "treating" (or "treat" or "treatment") as used herein includes prohibiting, restraining, slowing, stopping, or reversing the progression or severity of an existing symptom or disorder. The term "preventing" (or "prevent" or "prevention") as used herein refers to prohibiting, restraining, or inhibiting the incidence or occurrence of a symptom or disorder. As appreciated by one of skill in the art, physiological disorders may present as a "chronic" condition, or as an "acute" episode. Thus, the treatment of disorders contemplates both acute events and chronic conditions. In an acute event, compound is administered at the onset of symptoms and discontinued when the symptoms disappear, whereas a chronic condition is treated throughout the course of the disease.

Compounds of the present invention may be formulated as part of a pharmaceutical composition. As such, a pharmaceutical composition comprising a compound of Formula (I), or a pharmaceutically acceptable salt thereof, in combination with a pharmaceutically acceptable carrier, diluent or excipient is an important embodiment of the invention. Examples of pharmaceutical compositions and methods for their preparation are well known in the art. A compound of Formula (I), or a composition comprising a compound of Formula (I) may be administered by any route which makes the compound bioavailable, including oral and parenteral routes.

As used herein the term "effective amount" refers to the amount or dose of a compound of Formula (I) which, upon single or multiple dose administration to the patient, provides the desired effect in the patient under diagnosis or treatment. An effective amount can be readily determined by the attending diagnostician, as one skilled in the art, by considering a number of factors such as the species of mammal; its size, age, and general health; the specific disease involved; the degree or severity of the disease; the response of the individual patient; the particular compound administered; the mode of administration; the bioavailability characteristics of the preparation administered; the dose regimen selected; and the use of any concomitant medications.

The compounds and compositions of the present invention may be administered, or used in a medicament, either alone or in combination with conventional therapeutic agents used to a particular disorder. Where the compounds or compositions of the present invention are used as part of a combination, the compound or composition comprising Formula (I) may be administered either separately, or as part of a formulation comprising the therapeutic agent with which it is to be combined.

In particular, conventional therapeutic agents for the treatment of erectile dysfunction may be advantageously combined with the compounds of Formula (I), or compositions comprising a compound of Formula (I). Conventional agents for the treatment of erectile dysfunction include the phosphodiesterase type 5 (PDE5) inhibitors tadalafil (Cialis™), sildenafil citrate (Viagra™) and vardenafil hydrochloride (Levitra™). Thus, the present invention also provides a method of treating or preventing erectile dysfunction comprising administering to a patient in need thereof an effective amount of a compound of Formula (I), or a pharmaceutically acceptable salt thereof, in combination with an agent selected from the group consisting of tadalafil, sildenafil citrate, and vardenafil hydrochloride. More particularly, the present invention provides a method of treating or preventing erectile dysfunction comprising administering to a patient in need thereof an effective amount of a compound of Formula (I), or a pharmaceutically acceptable salt thereof, in combination with an agent selected from the group consisting of Cialis™, Viagra™ and Levitra™.

The present invention further provides a combination therapy formulation which comprises: (a) a compound of Formula (I); (b) one or more co-agents that are conventional for the treatment of erectile dysfunction selected from the group consisting of tadalafil, sildenafil citrate, and vardenafil hydrochloride; and optionally (c) a pharmaceutically acceptable carrier, diluent or excipient. More particularly, the present invention provides a combination therapy formulation which comprises: (a) a compound of Formula (I); (b) one or more co-agents that are conventional for the treatment of erectile dysfunction selected from the group consisting of Cialis™, Viagra™ and Levitra™; and optionally (c) a pharmaceutically acceptable carrier, diluent or excipient.

Particular Aspects of the Invention

The following list sets out several groupings of particular substituents and particular variables for compounds of Formula (I). It will be understood that compounds of Formula (I) having such particular substituents or variables, as well as methods and uses employing such compounds, represent particular aspects of the present invention.

Thus, a particular aspect of the present invention is a compound of Formula (I) wherein:

(a) R represents

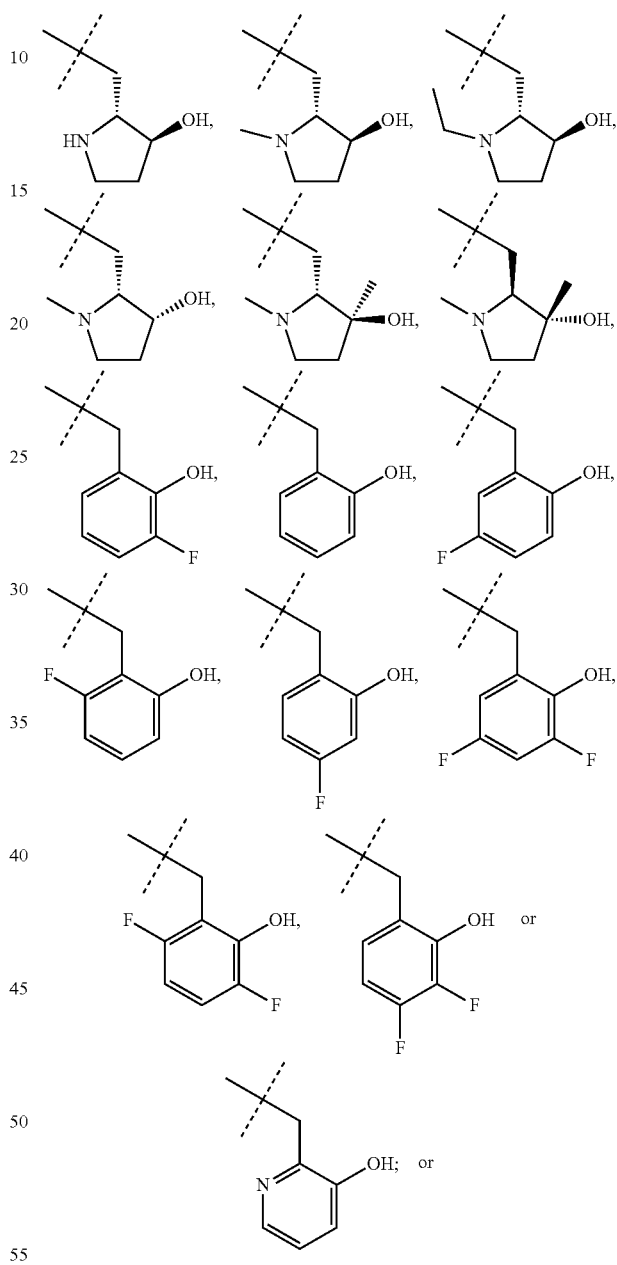

(b) R represents

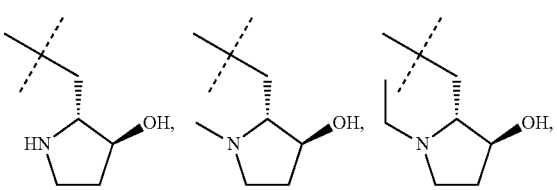

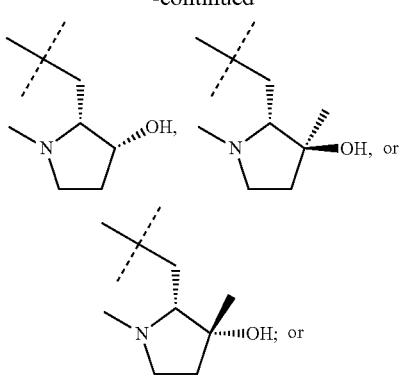
(c) R represents
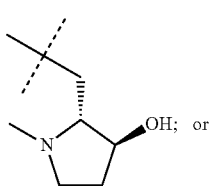
(d) R represents
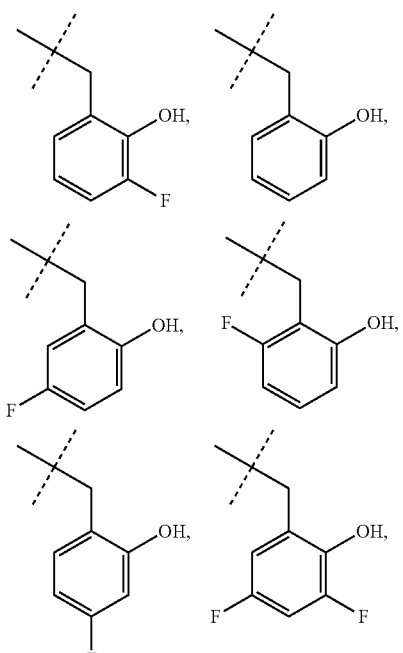
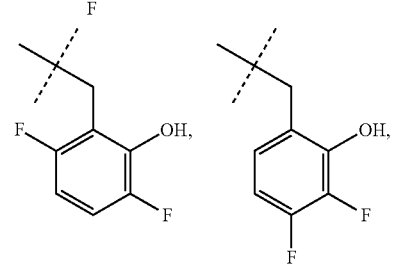
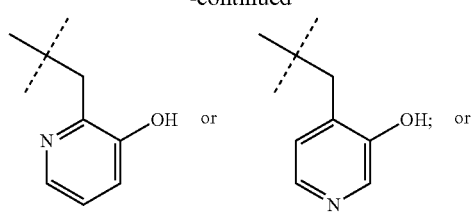
(e) R represents
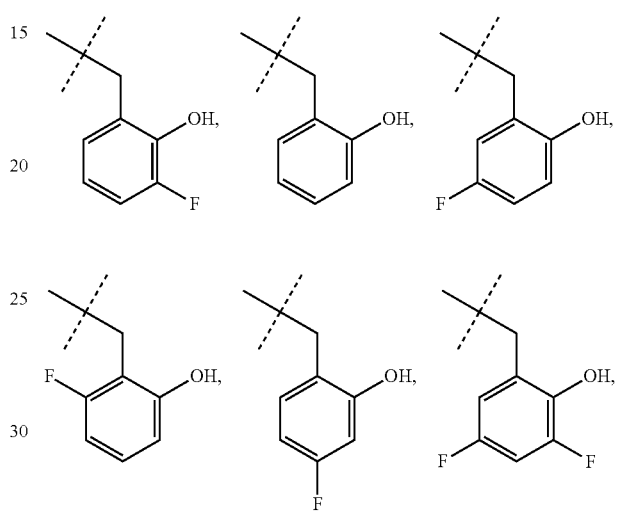
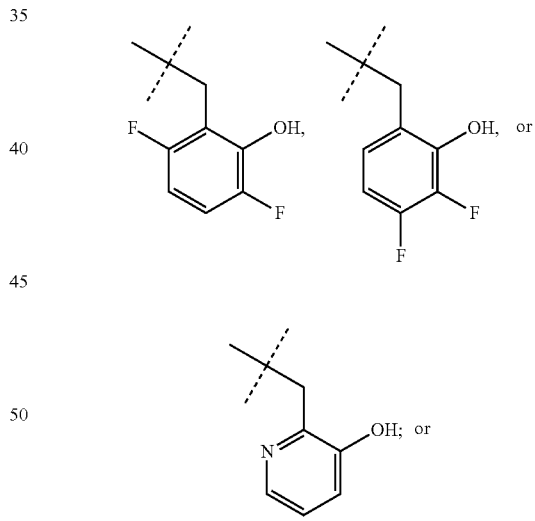
(f) R represents
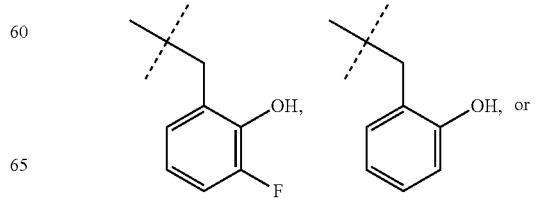

-continued

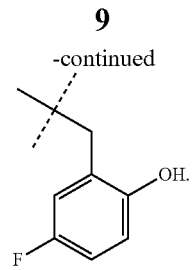

In addition, a most particular embodiment of the present invention is provided by those compounds of Formula (I) exemplified herein, and even more particularly the compounds [(S)-7-Cyano-4-((2R,3S)-3-hydroxy-1-methyl-pyrrolidin-2-ylmethyl)-1,2,3,4-tetrahydro-cyclopenta[b]indol-2-yl]-carbamic acid isopropyl ester, [(S)-7-cyano-4-(3-fluoro-2-hydroxybenzyl)-1,2,3,4-tetrahydrocyclopenta[b]indol-2-yl]-carbamic acid isopropyl ester, [(S)-7-Cyano-4-(2-hydroxy-benzyl)-1,2,3,4-tetrahydro-cyclopenta[b]indol-2-yl]-carbamic acid isopropyl ester, and [(S)-7-Cyano-4-(5-fluoro-2-hydroxy-benzyl)-1,2,3,4-tetrahydro-cyclopenta[b]indol-2-yl]carbamic acid isopropyl ester.

The compounds of formula (I) may be prepared by a variety of procedures known in the art as well as those described in the Schemes, Preparations, and Examples below. However, the following discussion is not intended to be limiting to the scope of the present invention in any way. For example, the specific synthetic steps for each of the routes described may be combined in different ways, or in conjunction with steps from different schemes, to prepare additional compounds of Formula (I).

The substituents, unless otherwise indicated, are as previously defined. The reagents and starting materials are readily available to one of ordinary skill in the art or may be made by procedures which are selected from standard techniques of organic and heterocyclic chemistry, techniques which are analogous to the syntheses of known structurally similar compounds, and the procedures described in the Examples below, including any novel procedures. As used herein, the following terms have the meanings indicated: "MeOH" refers to methanol; "EtOH" refers to ethanol; "i-PrOH" refers to isopropanol; "EtOAc" refers to ethyl acetate; "DMF" refers to dimethylformamide; "DMSO" refers to methyl sulfoxide; "NMP" refers to 1-methyl-2-pyrrolidinone; "TFA" refers to trifluoroacetic acid; "THF" refers to tetrahydrofuran; "DEAD" refers to diethyl azodicarboxylate; "DIAD" refers to diisopropyl diazodicarboxylate; "NBS" refers to N-bromosuccinimide; "t-boc" or "boc" refers to tert-butoxycarbonyl; "TBDMS" refers to t-butyldimethylsilyl; and "Ptg" refer to protecting group.

Scheme 1

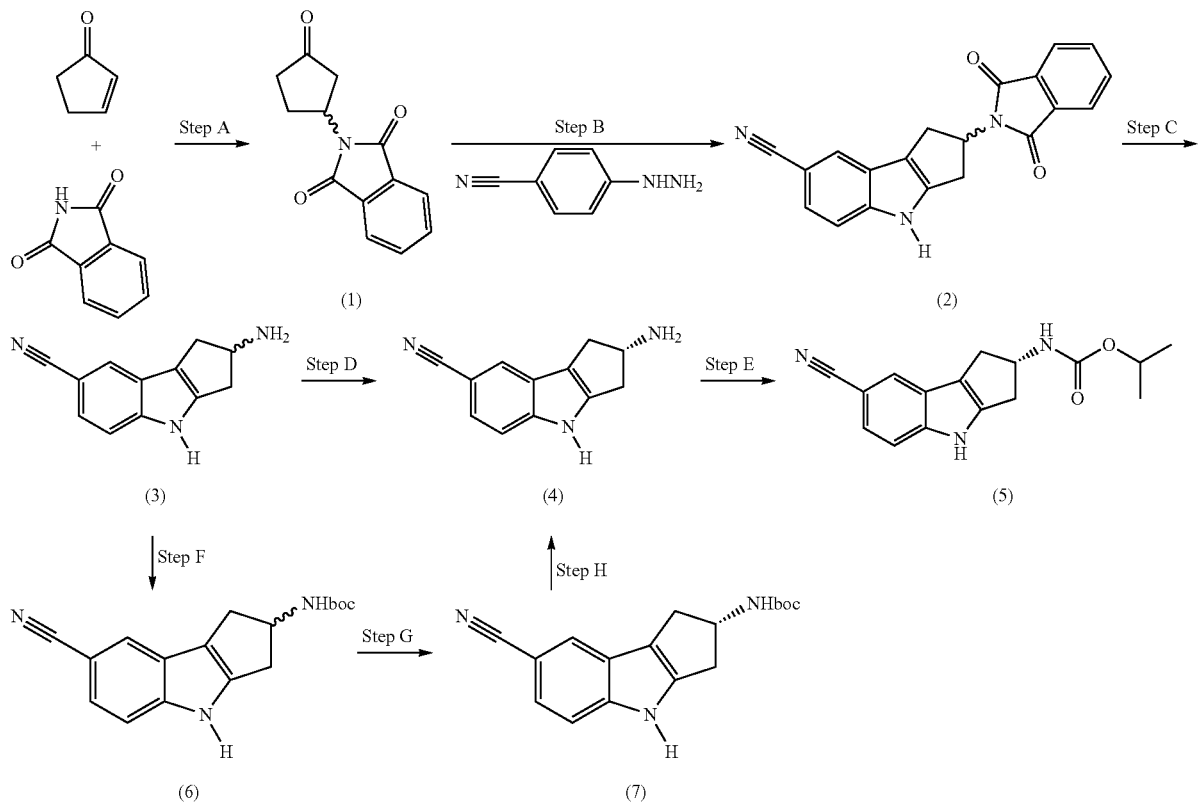

Formation of an intermediate of formula (5) can be carried out in accordance with reactions as depicted in Scheme 1.

In Scheme 1, Step A, cyclopentenone is reacted with phthalimide in a Michael addition to give (R,S)-2-(3-oxo-cyclopentyl)-isoindole-1,3-dione (1). The reaction is performed in methanol/2 N Na$_2$CO$_3$ in a ratio of 10/1 by volume preferably at ambient temperature using conditions similar to those described by O. Nowitzki, et. al. in *Tetrahedron* 1996, 52, 11799-11810. The product is isolated by addition of water and (1) obtained as a white solid.

In Step B, (R,S)-2-(3-oxo-cyclopentyl)-isoindole-1,3-dione (1) is reacted with 4-cyano-phenylhydrazine in a typical Fischer indole synthesis to give a tetrahydrocyclopenta[b]indole of formula (2). The skilled artisan will recognize that there are a variety of acidic conditions to effect a Fischer indole synthesis, including both proton and Lewis acids. The preferred conditions use a mixture of glacial acetic acid with 4 N HCl in dioxane, at a temperature of about 50° C. to the reflux temperature of the solvent, for about 4 to 24 hours. The product is isolated by addition of water followed by filtration of the resulting solid. The solid is sonicated in methanol to give material of sufficient purity. Alternatively, the reaction is effected using a Lewis acid, such as zinc chloride, in an amount of about 2 to 4 equivalents. Other preferred conditions for Step B use ethanol at reflux temperature for about 4 to 24 hours. The product is isolated and may be purified by filtration of the reaction mixture, followed by silica gel chromatography of the filtrate.

In Scheme 1, Step C, the phthalimide group of the tetrahydrocyclopenta[b]indole of formula (2) is cleaved with hydrazine or hydrazine hydrate to provide an aminotetrahydrocyclopenta[b]indole of formula (3) using conditions as described by M. Alajarín, et al (*Eur. J. Org. Chem.* 2002, 4222-4227). The reaction proceeds in a solvent mixture of tetrahydrofuran/ethanol in a ratio of about 5.5/1 by volume at a temperature of 0 to 50° C., preferably at about room temperature, for 4 to 72 hours. The resulting phthalhydrazide is removed by filtration and the product isolated by concentration of the filtrate. It may be purified by chromatography using techniques known in the art.

In Scheme 1, Step D, the racemic aminotetrahydrocyclopenta[b]indole of formula (3) is resolved to the chiral (S)-aminotetrahydrocyclopenta[b]indole of formula (4). The amine is dissolved in an appropriate solvent, such as ethanol and recrystallized as the salt of D-pyroglutamic acid. After isolation of the salt the free base of formula (4) is obtained by dissolution in water and adjustment of the pH to 9 using concentrated aqueous ammonia. The resulting solid is filtered to provide (S)-2-amino-1,2,3,4-tetrahydrocyclopenta[b]indole-7-carbonitrile (4) with specific rotation: $[a]_D^{25}$ −68.3° (MeOH).

In Step E, the amine of formula (4) is acylated with isopropyl chloroformate to give a carbamate of formula (5), using conditions well known to those skilled in the art. The amine is combined with an excess of an organic amine base such as triethylamine or diisopropylethylamine in an inert solvent such as tetrahydrofuran, toluene, dichloroethane or dichloromethane, N-methylpyrrolidinone, or N,N-dimethylformamide, or a mixture thereof. Preferred conditions use diisopropylethylamine in dichloromethane in the presence of isopropylchloroformate at a temperature of about 0 to 40° C. for 1 to 72 hours. The product is isolated by addition of water and diethyl ether, followed by stirring and collection of the resulting solid. If the product is sufficiently soluble in an appropriate organic solvent it may be isolated by extractive techniques.

Alternatively, as shown by Step F, the racemic amine of formula (3) is protected as the t-butoxycarbonyl (boc) protected amine of formula (6) using conditions common in the art. In Step G, the racemic mixture is then resolved using chiral chromatography to obtain the (S) enantiomer of formula (7). The boc group is then removed using typical acidic conditions with HCl or TFA to obtain the chiral amine of formula (4).

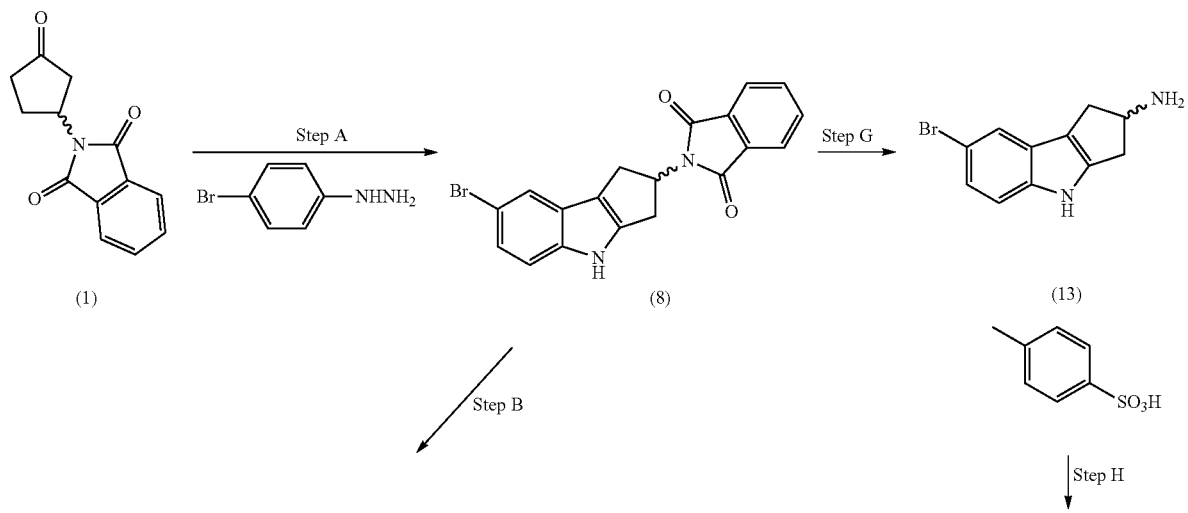

Scheme 2

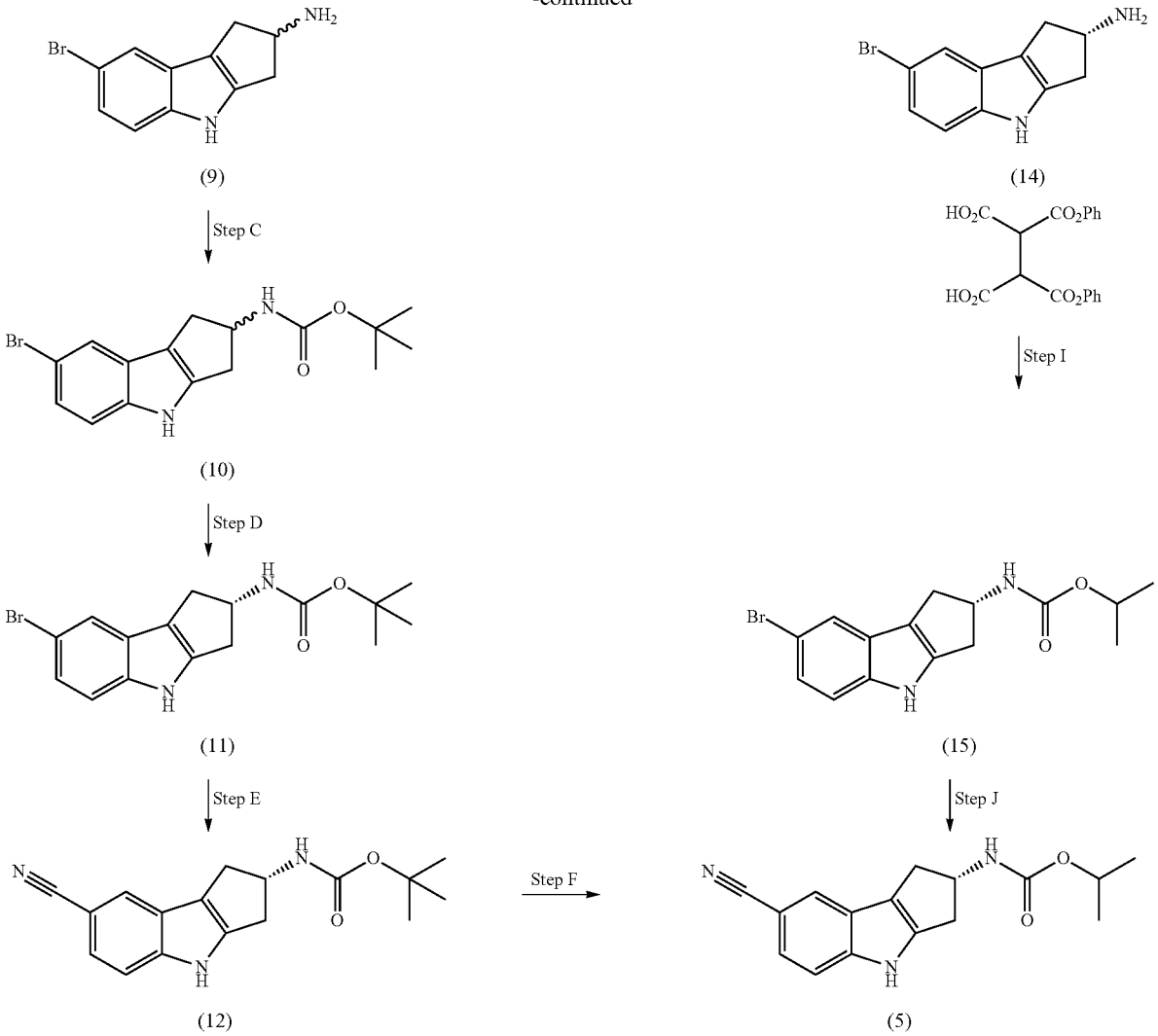

In Scheme 2 is depicted alternate syntheses for the intermediate of formula (5).

In Scheme 2, Step A, (R,S)-2-(3-oxo-cyclopentyl)-isoindole-1,3-dione (1) is reacted with 4-bromophenylhydrazine hydrochloride in a typical Fischer indole synthesis. Preferred conditions use glacial acetic acid at about 50 to 80° C. for 2 to 24 h.

In Step B, the phthalimide group of the tetrahydrocyclopenta[b]indole of formula (8) is cleaved with hydrazine or hydrazine hydrate to provide an aminotetrahydrocyclopenta[b]indole of formula (9). Preferred conditions use tetrahydrofuran/ethanol in a mixture of about 20/1 by volume at a temperature of about 40 to 70° C., for 1 to 12 hours. The resulting phthalhydrazide is removed by filtration and the product isolated by concentration of the filtrate.

In Scheme 2, Step C, the amine of formula (9) is protected with a t-boc group to give the protected amine of formula (10). Preferred conditions use di-tert-butyldicarbonate in an inert solvent such as THF or dioxane, in the presence of an inorganic base such NaHCO$_3$. In Step D, the racemic t-boc material of formula (10) is resolved using chiral HPLC to obtain the (S) enantiomer of formula (11).

In Step E, the (S) bromo carbamate of formula (11) is converted to the nitrile of formula (5). The reaction is run in an inert solvent, such as N,N'-dimethylacetamide in the presence of a mixture of zinc acetate or zinc formate, zinc cyanide, and zinc dust. A palladium catalyst is used, such as 1,1'-bis(diphenylphosphino)ferrocene)palladium (II) chloride. The reaction is heated at about 80 to 120° C. for about 2 to 24 h.

In Step F, the boc group is removed using typical acidic conditions such as HCl/dioxane or TFA to obtain the chiral amine of formula (4) (see Scheme 1) which is then acylated, as described in Scheme 1, Step E, with isopropyl chloroformate to give a carbamate of formula (5).

Alternatively, in Scheme 2, Step G, the phthalimide group of the tetrahydrocyclopenta[b]indole of formula (8) is cleaved with hydrazine or hydrazine hydrate to provide an aminotetrahydrocyclopenta[b]indole of formula (9) as previously described in Step B. Subsequently, the resulting free amine is converted to the p-toluenesulfonic acid salt in ethanol.

In Step H, the racemic aminotetrahydrocyclopenta[b]indole tosylate salt of formula (13) is freed and the resulting free amine is resolved using dibenzyl-D-tartaric acid to obtain the tartaric acid salt of the (S)-aminotetrahydrocyclopenta[b]indole of formula (14). The salt formation is preferably done in a solvent mixture of ethanol and water with reflux for about 1 to 6 hours, followed by cooling to obtain the desired enantiomer.

In Step I, the salt of formula (14) is neutralized to the free base and then acylated to obtain a carbamate of formula (15). The salt is neutralized with an inorganic base, such as sodium hydroxide solution. The free base is obtained by extraction followed by acylation with isopropyl chloroformate in the presence of an organic amine such as diisopropylethyl amine in an inert solvent or solvent mixture of tetrahydrofuran and methyl t-butyl ether.

In Scheme 2, Step J, the bromo carbamate of formula (15) is converted to the nitrile of formula (5) as previously described for Step E.

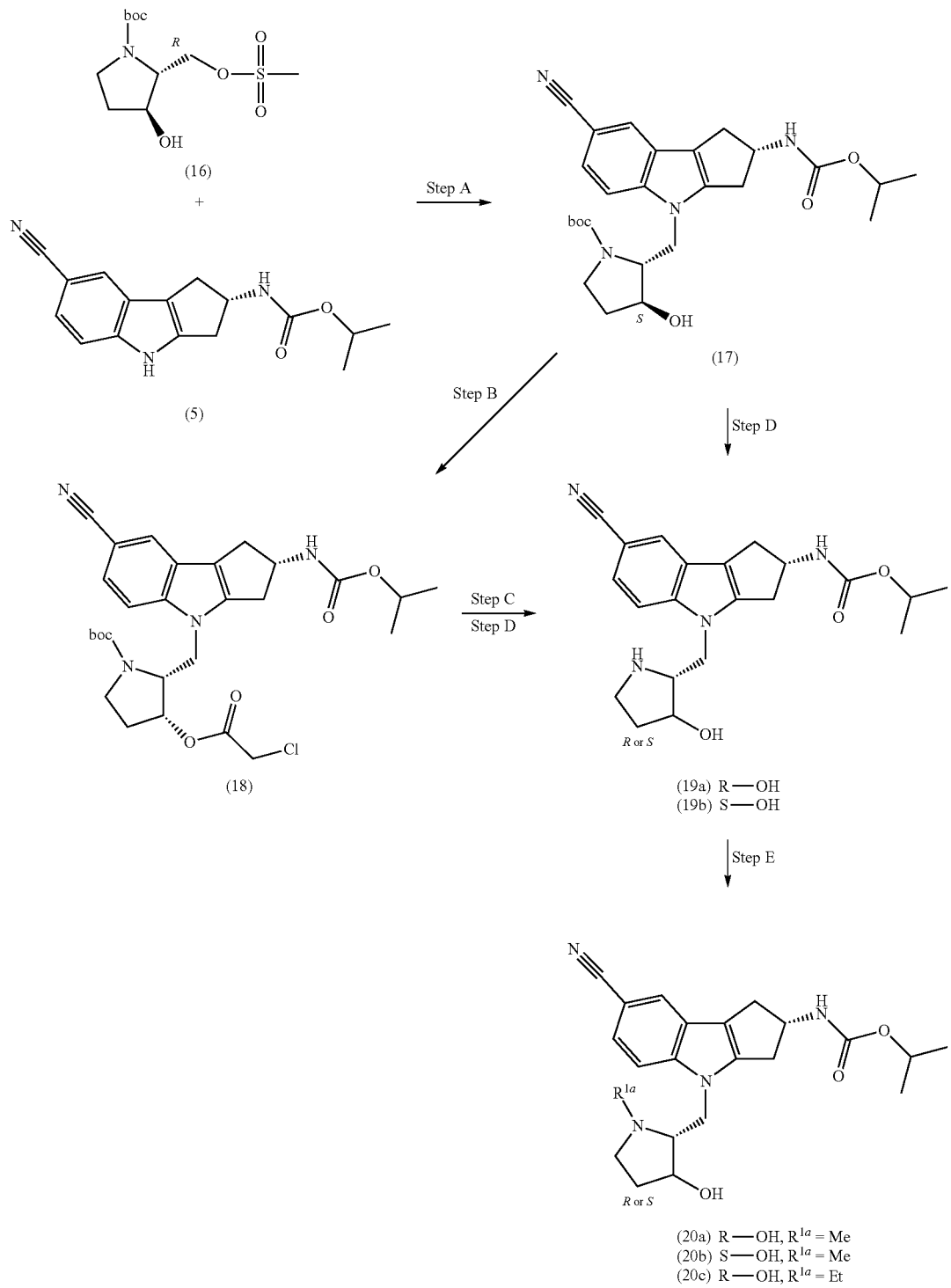

Scheme 3

Formation of compounds of the invention of formula (20a, b, or c) can be carried out in accordance with reactions as depicted in Scheme 3.

In Scheme 3, Step A, the cyano tetrahydrocyclopenta[b]indole of formula (5) is alkylated with the alkyl mesylate of formula (16) to provide the alkylated tetrahydrocyclopenta[b]indole of formula (17). The reaction proceeds in an inert solvent, such as DMF, in the presence of an inorganic base, such as cesium carbonate with addition of potassium iodide. The reaction proceeds at a temperature of about 50 to 100° C. for about 8 to 72 h.

In Scheme 3, Step B, the chirality of the hydroxyl group of the pyrrolidine of formula (17) is converted from (3S) to (3R). The chiral conversion is effected using a Mitsunobu reaction to give the chloroacetoxy pyrrolidine of formula (18). The skilled artisan will recognize that there are various Mitsunobu conditions employed in the art. For example, the alcohol of formula (17) is dissolved in a suitable anhydrous solvent like THF, $CH_2Cl_2$, or toluene and treated with a trialkyl- or triarylphosphine such as $Me_3P$, $Bu_3P$, or $Ph_3P$ and a dialkylazodicarboxylate, such as DEAD or DIAD.

In Step C, the 3R-chloroacetoxy pyrrolidine of formula (18) is hydrolyzed to the 3R-hydroxypyrrolidine of formula (19a). The hydrolysis is accomplished using an inorganic base, such as lithium hydroxide, in a solvent such as methanol, at 0 to 50° C. for 4 to 24 h. In Step D the boc protecting group is removed using acidic conditions such as TFA or preferably 4 N HCl in dioxane to provide the 3S-hydroxypyrrolidine of formula (19b).

In Scheme 3, Step E, the hydroxpyrrolidine of formula (19a or b) is alkylated using reductive amination conditions to give a N-alkyl pyrrolidine of formula (20a, b, or c). The reaction takes place in an inert solvent, such as THF, dichloromethane, or preferably, chloroform using a reducing reagent, such as sodium triacetoxyborohydride from about 0 to 50° C. for 8 to 24 h. The aldehyde used can be either formaldehyde or acetaldehyde to provide compounds of formula (20a, b, or c).

(2R,3S)-3-Hydroxy-2-methanesulfonyloxymethyl-pyrrolidine-1-carboxylic acid tert-butyl ester (16) can be readily prepared by methods similar to those described herein or by using procedures that are established in the art. For example, 3-hydroxy-L-proline can be protected with boc to give (2S,3S)-1-(tert-butoxycarbonyl)-3-hydroxypyrrolidine-2-carboxylic acid. The carboxylic acid is reduced to the alcohol and subsequently converted to the mesylate of formula (16).

Scheme 4

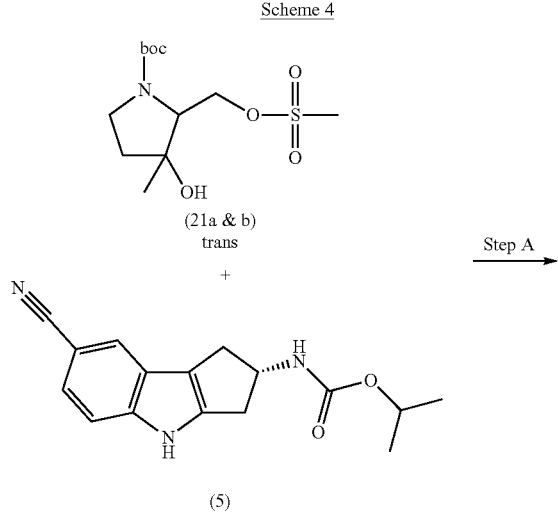

(21a & b)
trans

Step A

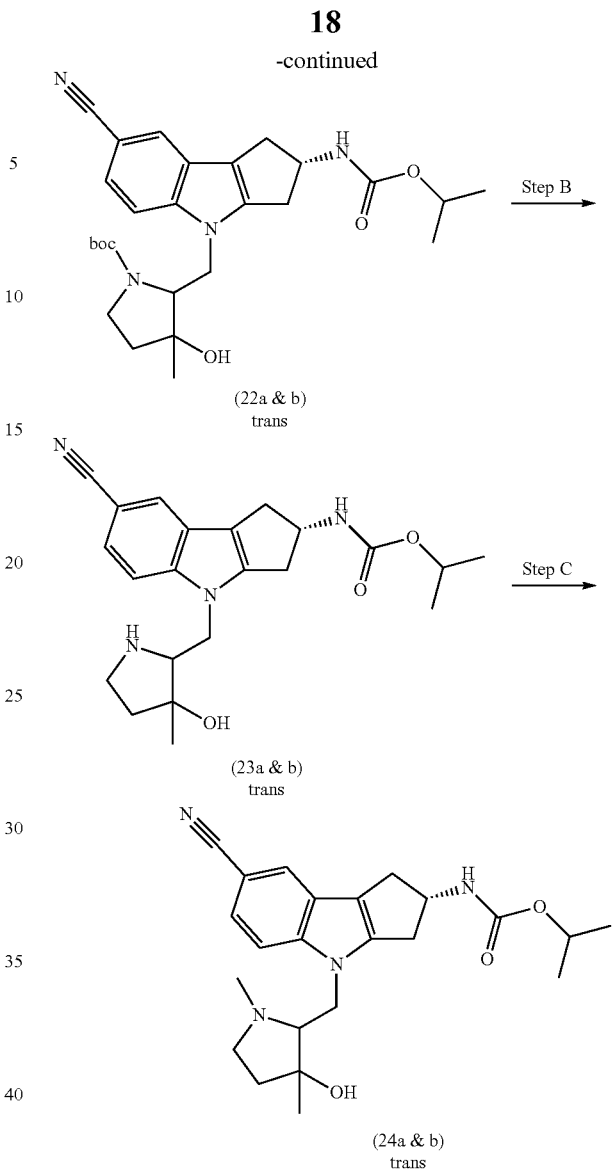

(22a & b)
trans

Step B (23a & b)
trans

Step C (24a & b)
trans

Formation of compounds of the invention of formula (24a & b) can be carried out in accordance with reactions as depicted in Scheme 4.

In Scheme 4, Step A, the cyano tetrahydrocyclopenta[b]indole of formula (5) is alkylated with the alkyl mesylate of formula (21a & b) to provide the alkylated tetrahydrocyclopenta[b]indole of formula (22a & b). The alkyl mesylate of formula (21a & b) is used as a mixture of the two trans enantiomers. The alkylation is preformed similarly to conditions described in Scheme 3, Step A, above.

In Step B the boc protecting group is removed using acidic conditions such as TFA or preferably 4 N HCl in dioxane.

In Scheme 4, Step C, the hydroxyproline of formula (23a & b) is alkylated using reductive amination conditions as previously described for Scheme 3, Step E to provide a mixture of the trans enantiomers as formula (24a & b). The enantiomers can be separated using chiral chromatography.

trans-3-Hydroxy-2-methanesulfonyloxymethyl-3-methyl-pyrrolidine-1-carboxylic acid tert-butyl ester (21a & b) can be readily prepared by methods similar to those described herein or by using procedures that are established in the art. For example, trans-2-benzyloxymethyl-3-methyl-pyrrolidin- 3-ol can be obtained by one-pot conversion of the appropriate 2,3-aziridin-1-ol (J. Schomaker and S. Bhattacharjee, *J. Am. Chem. Soc.*, 2007, 129, 1996-2003). The nitrogen of the pyrrolidinol is then protected with t-boc and the benzyl group removed by hydrogenation. The resulting alcohol is mesylated to give the trans enantiomers of formula (21a & b).

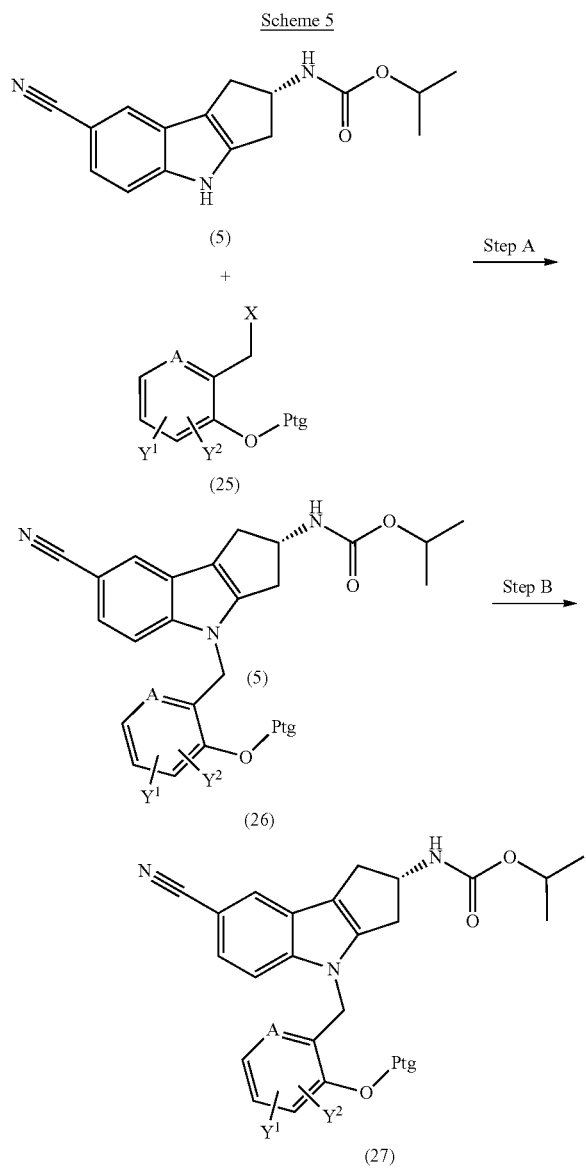

Scheme 5

If A = C then $Y^1$ = F, $Y^2$ = H or F
If A = N, then $Y^1$ = $Y^2$ = H
X = Cl or Br,
Ptg = Me or TBDMS Formation of compounds of the invention of formula (27) can be carried out in accordance with reactions as depicted in Scheme 5.

In Scheme 5, Step A, the cyano tetrahydrocyclopenta[b]indole of formula (5) is alkylated with the benzyl or pyridylmethyl halide of formula (25) to provide the alkylated tetrahydrocyclopenta[b]indole of formula (26). The phenyl or pyridyl ring is substituted with hydroxyl functionality, which is protected with protecting groups (Ptg) known in the art, for example as the methyl ether or silyl ether. The alkylation is performed similarly to conditions described in Scheme 3, Step A, above.

In Step B, the protecting group is removed to give the phenol or hydroxy pyridine of formula (27). For example the methyl ether is converted to the free hydroxyl by reaction with boron tribromide in an inert solvent such as dichloromethane at a temperature of about −20 to 25° C. Alternatively a silyl protecting group can be removed with fluoride anion using reagents such as cesium fluoride or preferably tetrabutylammonium fluoride.

The benzyl halides of formula (25) can be readily prepared by methods similar to those described herein or by using procedures that are established in the art. For example, fluoro or difluoro 2-hydroxy benzaldehydes can be alkylated with iodomethane to provide the 2-methoxy benzaldehyde. The benzaldehyde can be reduced to the corresponding benzyl alcohol and then converted to the (chloromethyl)-2 methoxybenzene of formula (25) wherein X=Cl and Ptg=Me. Alternatively, fluoro or difluoro 2-methylphenols can be silylated with t-butyldimethylchlorosilane followed by reaction with N-bromosuccinimide to obtain the benzyl bromide of formula (25), wherein X=Br and Ptg=TBDMS. 2-(Chloromethyl)-3-methoxypyridine can be obtained from 3-methoxy-2-picoline by chlorination with $POCl_3$.

Determination of Biological Activity:

As evidenced by in vitro and in vivo testing, exemplified compounds of Formula (I) possess profiles of activity which suggest they have utility in the treatment of disorders responsive to steroidal androgen therapy. In particular, exemplified compounds of Examples 1-10 and 12 of Formula (I) are potent AR ligands which agonize the androgen receptor. In addition, the exemplified compounds of Examples 1-10 and 12 of Formula (I) selectively bind to AR relative to each of MR, GR, and PR.

As used herein, "$K_d$" refers to the equilibrium dissociation constant for a ligand-receptor complex; "$K_i$" refers to the equilibrium dissociation constant for drug-receptor complex, and is an indication of concentration of drug that will bind to half the binding sites at equilibrium; "$K_b$" refers to the equilibrium dissociation constant for an antagonist-receptor complex; "IC50" refers to the concentration of an agent which produces 50% of the maximal inhibitory response possible for that agent or, alternatively, to the concentration of an agent which produces 50% displacement of ligand binding to the receptor; "EC50" refers to the concentration of an agent which produces 50% of the maximal response possible for that agent; and "ED50" refers to the dose of an administered therapeutic agent which produces 50% of the maximal response for that agent.

Steroid Hormone Nuclear Receptor Binding Assay:

Cell lysates from human embryonic kidney HEK293 cells overexpressing human MR (mineralocorticoid receptor), GR (glucocorticoid receptor), AR (androgen receptor), or PR (progesterone receptor) are used for receptor-ligand competition binding assays to determine $K_i$ values. Typical procedures are provided below Briefly, steroid receptor competition binding assays are run in a buffer containing 20 mM HEPES buffer (pH=7.6), 0.2 mM EDTA, 75 mM NaCl, 1.5 mM $MgCl_2$, 20% glycerol, 20 mM sodium molybdate, 0.2 mM DTT (dithiothreitol), 20 μg/mL aprotinin and 20 μg/mL leupeptin (assay buffer). Typically, steroid receptor binding assays include radio-labeled ligands, such as 0.25 nM [$^3$H]-aldosterone for MR binding, 0.3 nM [$^3$H]-dexamethasone for GR binding, 0.36 nM [$^3$H]-methyltrienolone for AR binding, and 0.29 nM [$^3$H]-methyltrienolone for PR binding, and either 20 μg 293-MR lysate, 20

μg 293-GR lysate, 22 μg 293-AR lysate, or 40 μg 293-PR lysate per well. Assays are typically run in 96-well format. Competing test compounds are added at various concentrations ranging from about 0.01 nM to 10 μM. Non-specific binding is determined in the presence of 500 nM aldosterone for MR binding, 500 nM dexamethasone for GR binding, or 500 nM methyltrienolone for AR and PR binding. The binding reactions (140 μL) are incubated overnight at 4° C., then 70 μL of cold charcoal-dextran buffer (containing per 50 mL of assay buffer, 0.75 g of charcoal and 0.25 g of dextran) is added to each reaction. Plates are mixed for 8 minutes on an orbital shaker at 4° C. The plates are then centrifuged at 3,000 rpm at 4° C. for 10 minutes. An aliquot of 120 μL of the binding reaction mixture is then transferred to another 96-well plate and 175 μL of Wallac Optiphase Hisafe 3™ scintillation fluid is added to each well. Plates are sealed and shaken vigorously on an orbital shaker. After an incubation of 2 hours, plates are read in a Wallac Microbeta counter.

The data are used to calculate an estimated IC50 and percentage inhibition at 10 μM. The Kd for [$^3$H]-aldosterone for MR binding, [$^3$H]-dexamethasone for GR binding, [$^3$H]-methyltrienolone for AR binding, or [$^3$H]-methyltrienolone for PR binding, is determined by saturation binding. The IC50 values for compounds are converted to Ki using the Cheng-Prusoff equation.

Following a protocol essentially as described above, the compounds of Examples 1-10 and 12 display a K$_i$ in the AR binding assay of ≦500 nM. Specifically, the compounds of Examples 1, 2, 6, and 9 displayed a Ki in the AR binding assay of about 51 nM, 11 nM, 13 nM, and 0.8 nM respectively, thus demonstrating that compounds within the scope of the present invention are potent ligands of human AR.

Functional Assays of Steroid Nuclear Hormone Receptor Modulation:

Androgens exerts their physiological effects through interaction with the androgen receptor. Following cytoplasmic binding of an androgen to AR, the ligand receptor complex translocates to the cell nucleus where it binds to hormone response elements on DNA to initiate expression of target genes. The effects of androgens may be characterized as anabolic or androgenic in nature. Anabolic (i.e. tissue building) effects of androgens include increasing muscle mass and strength and bone mass, whereas androgenic (i.e. masculinizing) effects include the development of male secondary sexual characteristics such as the internal reproductive tissues (i.e. prostate and seminal vesicle), the external genetalia (penis and scrotum), libido, and hair growth patterns.

To demonstrate the ability of compounds of the present invention to modulate the activity of steroid hormone receptors (i.e. either agonize, partially agonize, partially antagonize, or antagonize), bioassays are performed which detect functional modulation of target gene expression in cells transiently transfected with a nuclear receptor protein and a hormone response element-reporter gene construct. The solvents, reagents, and ligands employed in the functional assay are readily available from commercial sources, or can be prepared by one of ordinary skill in the art. The following provides typical procedures for nuclear hormone receptor functional assays.

A. Nuclear Hormone Receptor Panel Screen

Human embryonic kidney HEK293 cells are transfected with steroid hormone receptor and reporter gene plasmids using a suitable transfection reagent such as Fugene™. Briefly, the reporter plasmid containing two copies of probasin ARE and TK (thymidine kinase) promoter upstream of the luciferase reporter cDNA, is transfected into HEK293 cells with a plasmid constitutively expressing human androgen receptor (AR) using viral CMV (cytomegalovirus) promoter. The reporter plasmid containing two copies of GRE and TK promoter upstream of the luciferase reporter cDNA is transfected with a plasmid constitutively expressing either human glucocorticoid receptor (GR), human mineralocorticoid receptor (MR), or human progesterone receptor (PR) using viral CMV promoter. Cells are transfected in T150 cm flasks in DMEM media with 5% charcoal-stripped Fetal Bovine Serum (FBS). After an overnight incubation, transfected cells are trypsinized, plated in 96 well dishes in DMEM media containing 5% charcoal-stripped FBS, incubated for 4 hours and then exposed to various concentrations of test compounds ranging from about 0.01 nM to 10 μM. In the antagonist mode for the assays, low concentrations of agonist for each respective receptor are added to the media (0.08 nM aldosterone for MR, 0.25 nM dexamethasone for GR, 0.66 nM of methyltrienolone for AR, and 0.08 nM of promegestone for PR). After 24 hours incubation with test compounds, cells are lysed and luciferase activity is determined using standard techniques.

Data are fitted to a four parameter-fit logistic curve to determine EC50 values. The percentage efficacy (compounds with saturated maximum responses) or the percent maximum stimulation (compounds with maximum responses that do not saturate) are determined relative to maximum stimulation obtained with the following reference agonists: 30 nM aldosterone for MR assay, 100 nM methyltrienolone for AR assay, 30 nM promegestone for PR assay, and with 100 nM dexamethasone for GR assay. IC50 values are determined similarly using antagonist mode assay data. In the antagonist mode, percent inhibitions are determined by comparing test compound activity in the presence of low concentration of agonist (0.08 nM aldosterone for MR, 0.25 nM dexamethasone for GR, 0.66 nM of methyltrienolone for AR, and 0.08 nM of promegestone for PR) to the response produced by the same low concentration of agonist in the absence of test compound.

B. C2C12 AR/ARE Reporter Assay:

As an indicator of agonist activity in muscle tissue, the C2C12 AR/ARE reporter assay is performed. Briefly, mouse myoblast C2C12 cells are co-transfected using Fugene™ reagent. A reporter plasmid containing a GRE/ARE (glucocorticoid response element/androgen response element) and TK promoter upstream of the luciferase reporter cDNA, is transfected with a plasmid constitutively expressing human androgen receptor (AR) using viral CMV promoter. Cells are transfected in T150 cm$^2$ flasks in DMEM media with 4% charcoal stripped Fetal Bovine Serum (FBS). After a 5 hour incubation, transfected cells are trypsinized, plated in 96 well dishes in DMEM media containing 4% charcoal-stripped FBS, incubated for 2 h and then exposed to various concentrations of test compounds ranging from about 0.01 nM to 10 μM. After 48 h of incubations with compounds, cells are lysed and luciferase activity is determined by standard techniques. Data is fit to a 4 parameter-fit logistics to determine EC50 values. The % efficacy is determined versus maximum stimulation obtained with 10 nM methyltrienolone.

Functional assays of steroid hormone nuclear hormone receptor modulation similar to those described above can be readily designed by the ordinarily skilled artisan. Following a protocol essentially as described above, the compounds of Examples 1-10 and 12 display an EC50 in the C2C12 AR/ARE reporter assay of ≦2000 nM. Specifically, the compounds of Examples 1, 2, 6, and 9 displayed an EC50 in the C2C12 AR/ARE reporter assay of about 20, 1.0, 0.3, and 0.3 respectively, thus demonstrating that compounds within the scope of the present invention are agonists of human AR Model of Efficacy and Selectivity:

Male Sprague Dawley rats (24 weeks old) are castrated (gonadectomized or "GDX") according to approved procedures and allowed to waste for eight weeks. Age-matched sham-operated mice are also prepared Animals are housed in a temperature-controlled room (24° C.) with a reversed 12 hour light/dark cycle and water and food are available ad libitum.

Animals are randomized based on body weight prior to ascribing a test slot. Compounds of the present invention are administered daily by oral gavage to the castrated thirty two week old rats (body weight about 450-500 g) using a conventional vehicle such as 1% sodium carboxymethylcellulose (CMC)+0.25% Tween 80+0.05% AntiFoam® in sterile $H_2O$. Sham operated rats treated with vehicle alone are used as a treatment positive controls whereas castrated rats treated only with vehicle are used as treatment negative control.

Test animals are dosed daily over a two or eight week timeframe with, for example, 0.3, 1, 2, 3, or 6 mg/kg/day of a compound of the present invention. After the treatment period, animals are sacrificed and the wet weight of the Levator Ani (LA) muscle and the bulbocavernous muscle in each test group may determined and compared to the wet weight of the Levator Ani and the bulbocavernous muscle from the castrated, vehicle-only control group (after weighing, the bulbocavernous muscle may be flash frozen in liquid nitrogen for later use in measuring nitric oxide synthase mRNA, as described below) As an indicator of tissue selective activity, the wet weight of the prostate from test animals may be similarly compared to the wet weight of the prostate from the castrated, vehicle-only group.

Following a protocol essentially as described above using an eight week treatment period, studies with the compound of Example 2 produced the following results: Sham (vehicle only) showed a mean LA wet weight of about 0.255 g, a mean prostate wet weight of about 824.5 mg, and a mean bulbocavernous wet weight of about 0.93 g; the castrated/vehicle only animals showed a mean LA wet weight of about 0.094 g, a mean prostate wet weight of about 103.8 mg, and a mean bulbocavernous wet weight of about 0.362 g; the 0.3 mg/kg study groups showed a mean LA wet weight of about 0.137 g, a mean prostate wet weight of about 72.4 mg, and a mean bulbocavernous wet weight of about 0.476 g; the 1.0 mg/kg study groups showed a mean LA wet weight of about 0.182 g, a mean prostate wet weight of about 102.8 mg, and a mean bulbocavernous wet weight of about 0.582 g; the 3.0 mg/kg study groups showed a mean LA wet weight of about 0.205 g, a mean prostate wet weight of about 147.4 mg, and a mean bulbocavernous wet weight of about 0.698 g; and the 6.0 mg/kg study groups showed a mean LA wet weight of about 0.264 g, a mean prostate wet weight of about 271.8 mg, and a mean bulbocavernous wet weight of about 0.955 g.

Thus, treatment with the compound of Example 2 produced a dose dependent increase in Levator ani and bulbocavernous weights in comparison to the castrated control group.

In Vitro Assay of Erectile Activity

The nitric oxide synthase/cyclic guanosine monophosphate (NOS/cGMP) pathway is critical for erectile activity. NOS expression leads to nitric oxide (NO) generation which, in turn, promotes cGMP generation through activation of guanylyl cyclase. cGMP promotes protein kinase G (PKG) activity which mediates relaxation of corporal smooth muscle to facilitate penile erection. Evidence supports a role for androgens in regulating the expression and activity of NOS isoforms in the corpus cavernorsum in experimental animal models. Traish et al., *European Urology*, 52; 54-70 (2007). Thus, androgen receptor modulators, which are capable of increasing the expression of NOS isoforms, are believed to have a role in regulating penile erectile activity.

To determine the ability of compounds of the present invention to up-regulate the expression of NOS isoforms, the following in vitro methods may be employed.

RNA is isolated from frozen bulbous and corpus cavernosum tissues that are obtained at necropsy from castrated Sprague Dawley rats that are prepared and dosed essentially as described above for the Model of Efficacy and Selectivity. cDNA is synthesized from 2 μg of RNA using a high capacity cDNA kit according to the manufacturer's instructions.

Real-time quantitative PCR is then performed according to the fluorescent TaqMan® methodology (Applied Biosystems). Assays-on-Demand™ (Applied Biosystems) probes are used for the rat epithelial nitric oxide synthase transcript (eNOS) while probes are designed for the rat penile specific isoform of neuronal nitric oxide synthase (pnNOS) using probe designer software (Applied Biosystems). The probes are designed to span a 102 bp region of the rat neuronal nitric oxide synthase gene (pnNOS) that is specific to pnNOS (positions 2865-2967). MGB™ Primer sequences are 5'CCGGAACCCTTGCGTTT 3' (SEQ ID NO:1) (forward) and 5'CAGACTGTGGGCTTCAGAGTCA 3' (SEQ ID NO:2) (reverse) and the probe sequence is 5'CCCGTAAAGGGCCT 3' (SEQ ID NO:3) (FAM NFQ). Assays-on-Demand™ probe sets for the PPIB transcript are used as an internal control. PCR is performed on an ABI Prism 7700 Sequence Detection System at the following thermocycler conditions: 2 min. at 50° C., 10 min. at 95° C., and 40 cycles at 95° C. for 30 s, and 60° C. for 1 min. All reactions are carried out in triplicate.

Using procedures essentially as described herein, the compound of Example 2 shows a dose dependent increase in penile nitric oxide synthase (pnNOS) mRNA in the bulbocavernosum tissues obtained from castrated Sprague Dawley rats treated over an eight week timeframe. Specifically, the 0.3 mg/kg study groups showed pnNOS expression of about 97% of control; the 1.0 mg/kg study group showed pnNOS expression of about 93% of control; the 3.0 mg/kg study group showed pnNOS expression of about 153% of control; and the 6.0 mg/kg study group showed pnNOS expression of about 248% of control.

In addition, in a separate cohort, the compound of Example 2 shows an increase in epithelial nitric oxide synthase (eNOS) mRNA in the corpus cavernosum tissue obtained from castrated Sprague Dawley rats treated over a two week timeframe at 2 mg/kg/day. Specifically, eNOS expression in the study group was about 159% of control.

Reductions in muscle mass or strength may occur as a result of immobilization or disuse following, for example bone fractures or hip or knee replacements. In order to determine the ability of compounds of the present invention to treat or prevent loss of muscle mass or strength induced by immobilization, disuse or trauma, the following animal models may be employed.

Model of Muscle Loss Induced by Immobilization

A hind limb of Male 12 week ICR mice is immobilized in the plantar flexion mode by placing a cast on the limb. Following seven days of immobilization, the mice are treated with a daily administration of a compound of the present invention for various time periods. Control animals, with and without casts, are similarly treated with vehicle for various time periods. At the end of the treatment protocol, the mice are sacrificed, the wet weights of the casted gastrocnemius are determined and the individual treatment groups are compared to the vehicle controls. See generally *Am. J. Endocrinol. Metab.* 289: 969-980 (2005).

Model of Muscle Injury and Trauma

Male ICR mice are castrated at 8 weeks of age and allowed to waste for an additional 8 weeks. The mice are individually caged and maintained on a 12 hr light/dark cycle at 22° C. with ad lib access to food and water. Mice are anesthetized with isofluorane (1-5%) and the right gastrocnemius muscle is bilaterally injected with 100 μL of a 10 μM cardiotoxin (naja naja atra; Sigma Aldrich) to induce muscle injury. Animals recover from anesthesia and resume normal activity within 5 minutes. On day 5 post injection animals are treated with various doses of a compound of the present invention. After day 14 post injection, the treated mice are euthanized, weighed, and the gastrocnemius muscle tissue is harvested from both uninjected (contra-lateral control) and cardiotoxin injected legs. The muscle weights were matched to the uninjected and untreated control to establish percentage recovery from trauma.

To demonstrate that compounds of the present invention have the capacity to treat disorders associated with bone loss, such as osteoporosis or osteopenia, other animal models well known to those in the art may be employed. Examples of such models are provided in Y. L. Ma et al., *Japanese Journal of Bone and Mineral Metabolism* 23 (Suppl.): 62-68 (2005); Y. L. Ma et al., *Endocrinology* 144: 2008-2015 (2003); and K. Hanada et al., *Biol. Pharm. Bull.* 26(11): 1563-1569 (2003). Particular mention is made of the Female Rat Model of Estrogen Deficiency Osteopenia induced by Ovariectomy, and the Male Rat Model of Androgen Deficiency Osteopenia induced by Orchidectomy.

Model of Estrogen Deficiency Osteopenia Induced by Ovariectomy:

Six-month-old, virgin Sprague Dawley female rats weighing about 220 g are housed with ad libitum access to food and water. Bilateral ovariectomies (Ovx) are performed on the animals (except for sham-operated controls) and then randomized into treatment groups of 7-8 rats per group. Each assay typically contains at least 2 sets of controls, including sham-ovariectomy (Sham) and ovariectomized controls (Ovx) treated with vehicle. Ovx rats are permitted to lose bone for 1 month to establish osteopenia before treatment with test compound. Test compounds are administered orally via gavage to Ovx animals for 8 weeks. As a positive control, recombinant human PTH (1-38) (about 10 μg/kg/d, subcutaneously) may be given to a subset of Ovx animals. Following completion of the testing protocol, Quantitative computed tomographic (QCT) is used to analyze the volumetric bone mineral density (BMD, mg/cc) of lumbar vertebra L-5 and the femur. Biomechanical analyses of three point bending on the femoral midshaft and load to failure on the proximal femur are performed using a material mechanical testing machine and analyzed using TestWorks 4® software.

Model of Androgen Deficiency Osteopenia Induced by Orchidectomy:

Six-month-old, Sprague Dawley male rats weighing about 485 g are housed with ad libitum access to food and water. Bilateral orchidectomy (Orx) are performed on the animals (except for sham-operated controls) and then randomized into the treatment groups of 7-8 rats per group. Each assay typically contains at least 2 sets of controls, including sham-orchidectomized (Sham) and orchidectomized controls (Orx) treated with vehicle. Orx rats are permitted to lose bone for 2 months to establish osteopenia before treatment with test compound is initiated. Test compounds are administered orally via gavage to Ovx animals for 8 weeks. As a positive control, recombinant human PTH (1-38) (about 10 ug/kg/d, subcutaneously) may be given to a subset of Orx animals. Following completion of the testing protocol, the BMD of the vertebra and femur, as well as the biomechanical analyses of the femur may be performed as described above for the ovariectomized female rat model.

(See generally, Ma et al., *JBMR* 17:2256-2264 (2002), and Turner et al., *Bone* [Review] 14:595-608 (1993)).

As will be appreciated by one of ordinary skill in the art, the animal model protocols described above may be readily adapted for use in conjunction with the compounds and methods of the present invention.

The following preparations and examples further illustrate the invention and represent typical synthesis of the compounds of Formula (I), including any novel compounds, as described generally above. The reagents and starting materials are readily available to, or may be readily synthesized by, one of ordinary skill in the art. It should be understood that the Preparations and Examples are set forth by way of illustration and not limitation, and that various modifications may be made by one of ordinary skill in the art.

The R or S configuration of compounds of the invention may be determined by standard techniques such as X-ray analysis and correlation with chiral-HPLC retention time. The names of the compounds of the present invention are generally provided by Autonom 2000 for ISIS Draw add-in.

Preparation 1

(R,S)-2-(3-Oxo-cyclopentyl)-isoindole-1,3-dione

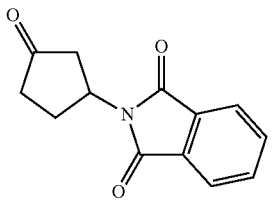 [SMILES: O=C1CCC(N2C(=O)c3ccccc3C2=O)C1]

While stirring vigorously with a mechanical stirrer, 2 M aqueous $Na_2CO_3$ (79 mL, 0.158 mol) is added to a slurry of cyclopentenone (100 g, 1.22 mol) and phthalimide (180 g, 1.22 mol) in MeOH (886 mL). After approximately 2 h, a thick white precipitate will form. The mixture is stirred at room temperature for 24 h. The white solid is collected by vacuum filtration and rinsed with methanol (1 L). The solid is suspended in water (1 L) and stirred for 3 h. The solid is collected and dried in a vacuum oven at 40° C. overnight to give 198 g (71%) of the title compound as a white solid. 1H NMR (DMSO-d6) δ 7.85-7.77 (m, 4H), 4.90 (m, 1H), 2.67 (ddd, 1H, J=18.5, 6.2, 1.3 Hz), 2.54 (dd, 1H, J=18.5, 9.2 Hz), 2.45 (m, 1H), 2.32-2.21 (m, 3H); ES/MS m/z 230 (M+1, weak). NOTE: The product will readily undergo the retro-Michael reaction upon treatment with aqueous base.

Preparation 2

(R,S)-2-(7-Bromo-1,2,3,4-tetrahydro-cyclopenta[b]indol-2-yl)-isoindole-1,3-dione

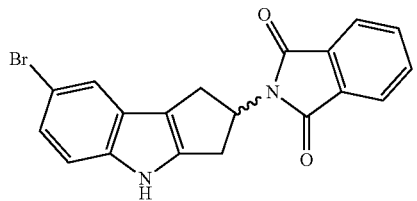 [SMILES: O=C1c2ccccc2C(=O)N1C1Cc2[nH]c3ccc(Br)cc3c2C1]

In a 5 L flask is mixed (R,S)-2-(3-oxo-cyclopentyl)-isoindole-1,3-dione (295.3 g, 1.29 mol), 4-bromophenyl hydrazine-HCl (287.9 g, 1.29 mol) and glacial acetic acid (3 L) with mechanical stirring. The reaction is refluxed for 5 h, and then cooled to room temperature. The reaction is poured into water (4 L) with rapid stirring. The solid is collected by vacuum filtration, washed with water (4 L) and air-dried for 30 min. The solid is slurried with MeOH (700 mL), collected by vacuum filtration and rinsed with MeOH (100 mL). The gray solid is air dried for 2 h, then dried overnight in a 50° C. vacuum oven to obtain 414.67 g (84%) of the title compound as a dark solid. ES/MS m/z ($^{79}$Br/$^{81}$Br) 381/383 [M+H]$^+$.

Preparation 3

(R,S)-7-Bromo-1,2,3,4-tetrahydro-cyclopenta[b]indol-2-ylamine

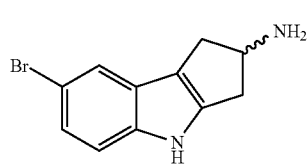 [SMILES: NC1Cc2[nH]c3ccc(Br)cc3c2C1]

To a solution of (R,S)-2-(7-bromo-1,2,3,4-tetrahydro-cyclopenta[b]indol-2-yl)-isoindole-1,3-dione (150 g, 393 mmol) in THF (1000 mL) and EtOH (150 mL) is added hydrazine monohydrate (35.0 g, 34.0 mL, 699 mmol). The reaction mixture is stirred with mechanical stirring at room temperature for 18 h and then for 2 h at 55° C., whereupon the reaction becomes very viscous and THF (425 mL) and EtOH (75 mL) are added. Heating at 55° C. is continued for another 2 h. The reaction is cooled to room temperature, filtered through diatomaceous earth, rinsed with THF, and concentrated to dryness. The residue is mixed with toluene and EtOH and concentrated again to dryness. The product is placed under high vacuum for 3 h, yielding 94 g (95%) of the title compound as a solid. LC-ES/MS m/z ($^{79}$Br/$^{81}$Br) 251/253 [M+H]$^+$, T$_R$=1.14 min.

Preparation 4

((R,S)-7-Bromo-1,2,3,4-tetrahydro-cyclopenta[b]indol-2-yl)-carbamic acid tert-butyl ester

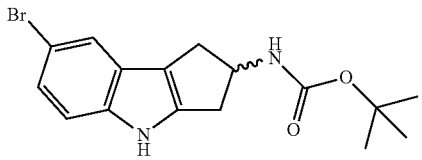 [SMILES: CC(C)(C)OC(=O)NC1Cc2[nH]c3ccc(Br)cc3c2C1]

A mixture of (R,S)-7-bromo-1,2,3,4-tetrahydro-cyclopenta[b]indol-2-ylamine (81.5 g, 325 mmol) in THF (800 mL) and saturated aqueous NaHCO$_3$ (200 mL) is treated with di-tert-butyldicarbonate (80.3 g, 357 mmol) portionwise and stirred at room temperature for one hour. The reaction is diluted with EtOAc (300 mL) and brine (100 mL). The layers are separated and the organic layer is dried over MgSO$_4$, filtered, and concentrated to a dark oily solid. The solid is mixed with CH$_2$Cl$_2$ (400 mL), cooled in an ice bath, and filtered. The solid is rinsed with CH$_2$Cl$_2$ and hexanes to recover 28.1 g (34%) of the title compound as a solid. An additional 78.8 g (60%) of the title compound is obtained by concentrating the filtrate and purifying by chromatography (1 L silica gel, loaded as a concentrated CH$_2$Cl$_2$ solution and eluted with 30% hexanes/CH$_2$Cl$_2$, 100% CH$_2$Cl$_2$, then 3% EtOAc/CH$_2$Cl$_2$). $^1$H-NMR (400 MHz, CDCl$_3$) δ 7.98-7.91 (m, 1H), 7.54 (s, 1H), 7.25 (s, 2H), 7.20-7.15 (m, 2H), 5.05-5.02 (m, 2H), 3.37-3.29 (m, 2H), 2.77-2.70 (m, 1H), 2.62-2.57 (m, 1H), 1.46 (s, 9H).

Preparation 5

((S)-7-Bromo-1,2,3,4-tetrahydro-cyclopenta[b]indol-2-yl)-carbamic acid tert-butyl ester

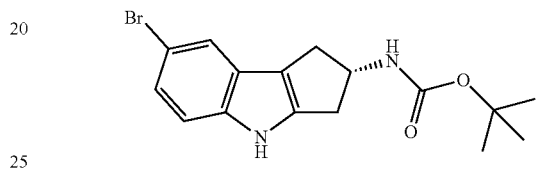

((R,S)-7-Bromo-1,2,3,4-tetrahydro-cyclopenta[b]indol-2-yl)-carbamic acid tert-butyl ester (635 g, 1810 mmol) is first triturated with cold Et$_2$O and then purified by chiral HPLC (column: Chiralcel OJ 8×32 cm; eluent: 100% MeOH) to afford 310 g of the title compound (second-eluting isomer) as a tan solid. Chiral HPLC OJ-H, 100% MeOH, UV detection @ 250 nm T$_R$=7.6 min, 97.8% ee.

Preparation 6

((S)-7-Cyano-1,2,3,4-tetrahydro-cyclopenta[b]indol-2-yl)-carbamic acid tert-butyl ester

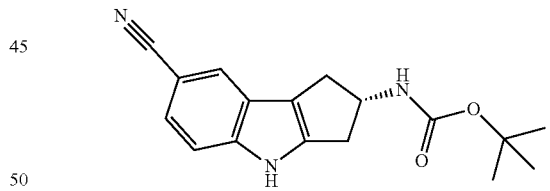

The following reagents are stirred together in DMF (250 mL) at 100° C. for 18 h: ((S)-7-bromo-1,2,3,4-tetrahydro-cyclopenta[b]indol-2-yl)-carbamic acid tert-butyl ester (50.0 g, 142 mmol), zinc cyanide (11.9 g, 99.7 mmol), zinc acetate (5.22 g, 28.5 mmol), 1,1'-bis(diphenylphosphino)ferrocene) palladium (II) chloride (Pd(dppf)$_2$Cl$_2$) (1.74 g, 2.14 mmol), and zinc (3.72 g, 56.9 mmol). The reaction is concentrated to dryness and partitioned between water and ethyl acetate. The organics are washed with water and brine, then concentrated to afford a solid. The solid is chromatographed in two equal portions on silica gel (1600 mL) as follows: load as a solution in CH$_2$Cl$_2$ and elute with 2% EtOAc in CH$_2$Cl$_2$ (3 L), then 5% EtOAc in CH$_2$Cl$_2$. The product is recovered from the two columns to give 29 g (69%) of the title compound as a white solid. $^1$H-NMR (400 MHz, CDCl$_3$) δ 8.39 (s, 1H), 7.74 (s, 1H), 7.34 (d, J=1.8 Hz, 2H), 5.05-4.96 (m, 2H), 3.37-3.25 (m, 2H), 2.80-2.63 (m, 2H), 1.46 (s, 9H).

Preparation 7

((S)-7-Cyano-1,2,3,4-tetrahydro-cyclopenta[b]indol-2-yl)-carbamic acid isopropyl ester

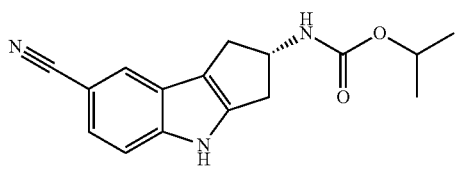 [SMILES: CC(C)OC(=O)N[C@@H]1Cc2[nH]c3ccc(C#N)cc3c2C1]

((S)-7-Cyano-1,2,3,4-tetrahydro-cyclopenta[b]indol-2-yl)-carbamic acid tert-butyl ester (10 g, 33.63 mmol) is dissolved in 1,4-dioxane (102 mL) and treated with 4 M HCl/dioxane (102 mL) at room temperature. After 18 h a solid is filtered off and washed with Et$_2$O (50 mL) and then dried in vacuo.

The solid is slurried in dichloromethane (168 mL) and treated with diisopropylethylamine (9.13 g, 12.3 mL, 70.1 mmol) and isopropyl chloroformate (1.0 M in toluene, 34.0 mL, 34.0 mmol) at room temperature. After 4 h the reaction is treated with water (50 mL) and concentrated to give an aqueous slurry of the product. The reaction is further diluted with water (500 mL) and sonicated for 15 min in an ultrasonic bath. A tan solid is filtered off and dried in vacuo at 40° C. The solid is slurried in Et$_2$O (100 mL), sonicated for 10 min in an ultrasonic bath, filtered, washed with Et$_2$O (50 mL), and then dried in vacuo to give 8.20 g (86% yield) of the title compound as a tan solid. LC-ES/MS m/z 284 [M+H]$^+$, 282 [M-H]$^-$, T$_R$=2.20 min; $^1$H-NMR (400 MHz, DMSO-d$_6$) δ 11.44 (s, 1H), 7.78 (s, 1H), 7.52 (d, J=7.5 Hz, 1H), 7.39 (d, J=8.4 Hz, 1H), 7.28 (dd, J=1.8, 8.4 Hz, 1H), 4.77-4.63 (m, 2H), 3.18-3.04 (m, 2H), 2.70 (dd, J=6.2, 15.8 Hz, 1H), 2.58 (dd, J=6.2, 14.5 Hz, 1H), 1.13 (d, J=6.2 Hz, 6H).

Preparation 8

(2S,3S)-1-(tert-butoxycarbonyl)-3-hydroxypyrrolidine-2-carboxylic acid

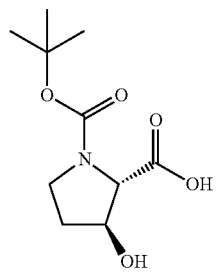 [SMILES: CC(C)(C)OC(=O)N1CC[C@H](O)[C@H]1C(=O)O]

A suspension of trans-3-hydroxy-L-proline (5 g, 37.56 mmol) in methanol (100 mL) is treated with diisopropylethylamine (6.55 mL, 37.56 mmol) and subsequently di-t-butyl-dicarbonate (8.87 g, 39.44 mmol) at room temperature. The resulting suspension is stirred for 2 h at room temperature while becoming a homogeneous solution. The solvent is removed in vacuo and the residue is dissolved in ethyl acetate (120 mL). The organic solution is washed with 1 N aqueous hydrogen chloride. The aqueous layer is discarded and the organic layer is washed with brine, dried over sodium sulfate, concentrated, and dried under vacuum to give 8.0 g (90%) of the title compound. $^1$H NMR (300 MHz, CDCl$_3$) δ 12.60 (s, br, 1H), 5.40 (s, br, 1H), 4.20-4.12 (m, 1H), 3.87 (d, J=6.4 Hz, 1H), 3.25-3.42 (m, 2H), 1.90-1.75 (s, br, 1H), 1.74-1.65 (s, br, 1H), 1.30 (d, J=7.1 Hz, 9H).

Preparation 9

(2R,3S)-tert-butyl-3-hydroxy-2-(hydroxymethyl)pyrrolidine-1-carboxylate

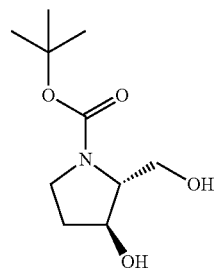

A solution of 3-hydroxy-pyrrolidine-1,2-dicarboxylic acid 1-tert-butyl ester (13.29 g, 57.47 mmol) in tetrahydrofuran (130 mL) is treated with borane-methyl sulfide complex (16.06 mL, 172.41 mmol) dropwise and stirred overnight at room temperature. The mixture is cooled to 5° C. in a water ice bath and treated with 3 N aqueous hydrogen chloride solution (5 mL) dropwise until evolution of gas has ceased. The resulting suspension is stirred further for 30 min and diluted with 5 N aqueous sodium hydroxide solution until a white solid is dissolved. This is extracted with ethyl acetate (3×100 mL). The organic layer is washed with water (2×100 mL) and brine, dried over sodium sulfate, filtered, and concentrated to dryness. The resulting oil is dried under vacuum to give 10.03 g (80%) of the title compound. LC-ES/MS m/z 457.2 [2M+Na]$^+$, T$_R$=1.59 min.

Preparation 10

(2R,3S)-3-Hydroxy-2-methanesulfonyloxymethyl-pyrrolidine-1-carboxylic acid tert-butyl ester

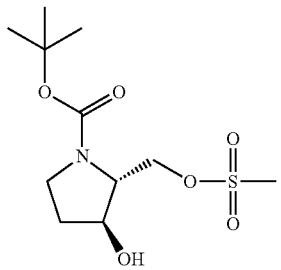 [SMILES: CC(C)(C)OC(=O)N1CC[C@H](O)[C@H]1COS(C)(=O)=O]

A suspension of (2R,3S)-tert-butyl 3-hydroxy-2-(hydroxymethyl)pyrrolidine-1-carboxylate (5.04 g, 23.20 mmol) and dibutyloxostannane (7.07 g, 27.84 mmol) in toluene (50 mL) is refluxed in a 130° C. oil bath for 2 h. The mixture is cooled to 0° C. in an ice bath for 30 min and treated with methanesulfonyl chloride (2.15 mL, 27.84 mmol) at once. The reaction is stirred for 30 min at 0° C. and then the mixture allowed to gradually warm to ambient temperature overnight. The solution is concentrated and the resulting residue purified by medium pressure liquid chromatography, eluting with ethyl acetate:hexane (8:2). Fractions containing pure product are combined and concentrated to give 6.14 g (96%) of dense oil as the title compound. LC-ES/MS m/z 318.2 [M+Na]+, $T_R$=2.34 min.

Preparation 11

(2R,3S)-2-((S)-7-Cyano-2-isopropoxycarbony-lamino-2,3-dihydro-1H-cyclopenta[b]indol-4-ylmethyl)-3-hydroxy-pyrrolidine-1-carboxylic acid tert-butyl ester

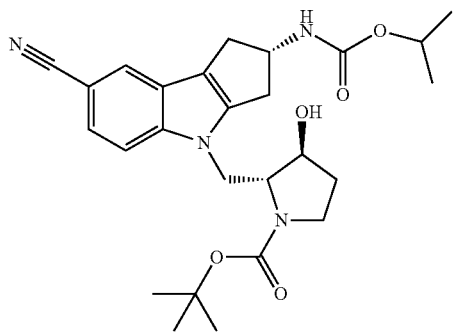 [SMILES: CC(C)OC(=O)N[C@H]1Cc2c(n(C[C@@H]3[C@@H](O)CCN3C(=O)OC(C)(C)C)c3ccc(C#N)cc23)C1]

A mixture of ((S)-7-cyano-1,2,3,4-tetrahydro-cyclopenta[b]indol-2-yl)-carbamic acid isopropyl ester (1.50 g, 5.29 mmol), (2R,3S)-3-hydroxy-2-methanesulfonyloxymethyl-pyrrolidine-1-carboxylic acid tert-butyl ester (3.13 g, 10.59 mmol), cesium carbonate (3.45 g, 10.59 mmol), and potassium iodide (88 mg, 529 μmol) in dimethylformamide (50 mL) is heated in a 60° C. oil bath for two days. After cooling to ambient temperature, the reaction is diluted with ethyl acetate (120 mL) and washed with water (3×100 mL) and brine. The organic portion is dried over sodium sulfate, filtered, and concentrated to dryness. The resulting residue is purified by medium pressure liquid chromatography, eluting with ethyl acetate:chloroform (2:8). Fractions containing pure product are combined and concentrated to afford 1.59 g (62%) of the title compound. LC-ES/MS m/z 505.2 [M+Na]+, $T_R$=3.97 min.

Preparation 12

(2R,3R)-3-(2-Chloro-acetoxy)-2-((S)-7-cyano-2-isopropoxycarbonylamino-2,3-dihydro-1H-cyclopenta[b]indol-4-ylmethyl)-pyrrolidine-1-carboxylic acid tert-butyl ester

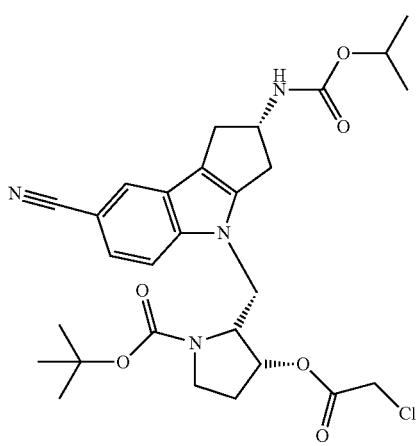

A mixture of (2R,3S)-2-((S)-7-cyano-2-isopropoxycarbo-nylamino-2,3-dihydro-1H-cyclopenta[b]indol-4-ylmethyl)-3-hydroxy-pyrrolidine-1-carboxylic acid tert-butyl ester (950 mg, 1.97 mmol), chloroacetic acid (227 mg, 2.36 mmol), and triphenylphosphine (626 mg, 2.36 mmol) in tetrahydrofuran (20 mL) is treated with diethyl azodicarboxylate (374 μL, 2.36 mmol) dropwise at room temperature. The reaction mixture is stirred overnight. The reaction is diluted with ethyl acetate (50 mL) and then washed with water and brine. The organic portion is dried over sodium sulfate and concentrated. The resulting residue is purified by medium pressure liquid chromatography, eluting with ethyl acetate:hexane (1:1). Fractions containing pure product are combined and concentrated to afford 0.59 g (54%) of the title compound. LC-ES/MS m/z 581.0 [M+Na]+, $T_R$=4.46 min.

Preparation 13

[(S)-7-Cyano-4-((2R,3R)-3-hydroxy-pyrrolidin-2-ylmethyl)-1,2,3,4-tetrahydro-cyclopenta[b]indol-2-yl]-carbamic acid isopropyl ester hydrochloride

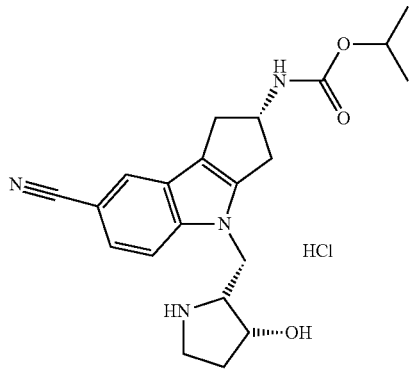

A solution of (2R,3R)-3-(2-chloro-acetoxy)-2-((S)-7-cyano-2-isopropoxycarbonylamino-2,3-dihydro-1H-cyclopenta[b]indol-4-ylmethyl)-pyrrolidine-1-carboxylic acid tert-butyl ester (500 mg, 894.4 μmol) in MeOH (2 mL) is treated with 2 N LiOH solution (2 mL) and the suspension is stirred for 4 h at room temperature. The suspension is diluted with ethyl acetate (60 mL) and washed with water and brine. The organic portion is dried over sodium sulfate, filtered, and concentrated. The residue (0.39 g) is dissolved in 10 mL of MeOH (10 mL) and treated with 4 N HCl in 1,4-dioxane solution (10 mL). The solution is stirred for 2 h and concentrated in vacuo to afford 0.37 g (92%) of the title compound. LC-ES/MS m/z 383.2 [M+H]+, $T_R$=1.86 min.

Preparation 14 trans-2-Benzyloxymethyl-3-hydroxy-3-methyl-pyrrolidine-1-carboxylic acid tert-butyl ester

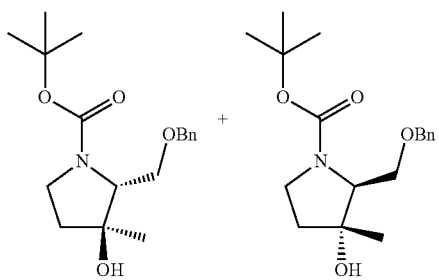 [SMILES: CC(C)(C)OC(=O)N1CC[C@](C)(O)[C@H]1COCc1ccccc1 ; CC(C)(C)OC(=O)N1CC[C@@](C)(O)[C@@H]1COCc1ccccc1]

A solution of trans-1-benzenesulfonyl-2-benzyloxymethyl-3-methyl-pyrrolidin-3-ol (13.42 g, 35.74 mmol) (J. Schomaker and S. Bhattacharjee, *J. Am. Chem. Soc.*, 2007, 129, 1996-2003) in anhydrous methanol (100 mL) is treated with magnesium turnings (5.26 g, 214.4 mmol) and sonicated for 45 min in a water bath. The resulting cloudy suspension is stirred in 40° C. oil bath for 20 h. Silica gel (30 mL) is added to the reaction mixture and diluted with methanol (50 mL) until the suspension is mixable. The suspension is stirred for 30 min and concentrated. The residue is dried under vacuum overnight. The silica residue was loaded to a DASI®65 cartridge, eluting with chloroform:methanol:aqueous ammonia (90:9:1). The starting trans-1-benzensulfonyl-2-benzyloxymethyl-3-methyl-pyrrolidin-3-ol (4.0 g) is obtained as well as the desired deprotected material (5.47 g). Dissolve the deprotected material in tetrahydrofuran (20 mL) and treat with di-t-butyl dicarbonate (5.7 g, 26.1 mmol). The solution is stirred for one hour and concentrated. The residue is diluted with ethyl acetate (100 mL) and washed with 0.5 N aqueous sodium hydroxide (50 mL) and brine. The organic portion is dried over sodium sulfate, filtered, and concentrated. The resulting residue is purified by medium pressure liquid chromatography, eluting with ethyl acetate:hexane (1:1). Fractions containing pure product are combined and concentrated to afford 8.15 g (71%) of the title compound. LC-ES/MS m/z 344.2 [M+Na]$^+$, $T_R$=3.71 min.

Preparation 15 trans-3-Hydroxy-2-hydroxymethyl-3-methyl-pyrrolidine-1-carboxylic acid tert-butyl ester

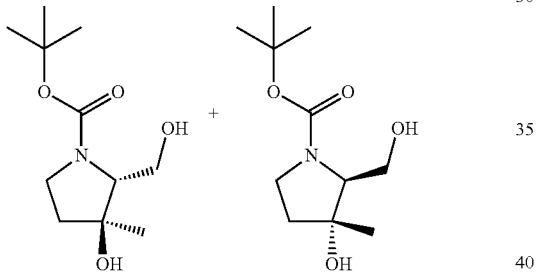

A solution of trans-3-hydroxy-2-hydroxymethyl-3-methyl-pyrrolidine-1-carboxylic acid tert-butyl ester (8.12 g, 25.26 mmol) in methanol (100 mL) is treated with 5% palladium over charcoal (50% wet, 3 g, 28.19 mmol) and hydrogenated at 350 kPa overnight. The catalyst is removed by filtration and the filtrate is concentrated. The resulting oil is dried under vacuum to give 5.8 g (99%) of the title compound. GC-MS m/z 231 [M]$^+$.

Preparation 16 trans-3-Hydroxy-2-methanesulfonyloxymethyl-3-methyl-pyrrolidine-1-carboxylic acid tert-butyl ester

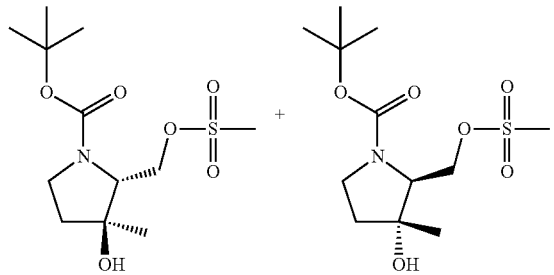 [SMILES: CC(C)(C)OC(=O)N1CC[C@](C)(O)[C@H]1COS(C)(=O)=O ; CC(C)(C)OC(=O)N1CC[C@@](C)(O)[C@@H]1COS(C)(=O)=O]

A mixture of trans-3-hydroxy-2-methanesulfonyloxymethyl-3-methyl-pyrrolidine-1-carboxylic acid tert-butyl ester (2.69 g, 11.63 mmol) and triethylamine (1.78 mL, 12.79 mmol) in dichloromethane (100 mL) is cooled in an acetonitrile/dry-ice bath (−40° C.) for 30 min and treated with methanesulfonyl chloride (945.21 µL, 12.21 mmol) at once. The solution is stirred for one hour at −40° C. and poured into a separatory funnel containing dichloromethane (50 mL) and water (100 mL). The organic solution is washed with water and brine, dried over sodium sulfate, filtered, and concentrated. The residue is purified by medium pressure liquid chromatography, eluting with ethyl acetate:hexane (8:2). Fractions containing pure product are combined and concentrated to afford 3.30 g (91%) of the title compound. LC-ES/MS m/z 640.6 [2M+Na]$^+$, $T_R$=2.27 min.

Preparation 17 trans-2-((S)-7-Cyano-2-isopropoxycarbonylamino-2,3-dihydro-1H-cyclopenta[b]indol-4-ylmethyl)-3-hydroxy-3-methyl-pyrrolidine-1-carboxylic acid tert-butyl ester

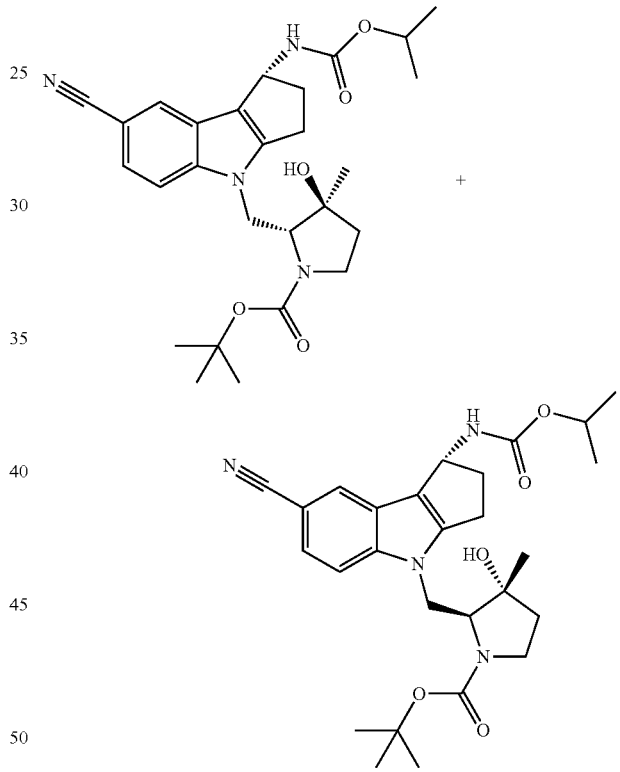

A mixture of ((S)-7-cyano-1,2,3,4-tetrahydro-cyclopenta[b]indol-2-yl)-carbamic acid isopropyl ester (2.00 g, 7.06 mmol), trans-3-hydroxy-2-methanesulfonyloxymethyl-3-methyl-pyrrolidine-1-carboxylic acid tert-butyl ester (3.28 g, 10.59 mmol), cesium carbonate (5.11 g, 15.53 mmol), and potassium iodide (118 mg, 705.9 µmol) in dimethylformamide (40 mL) is stirred under an argon atmosphere in a 60° C. oil bath for 48 h. The resulting suspension is cooled to room temperature and diluted with ethyl acetate (120 mL), then washed with water (3×100 mL) and brine. The organic portion is dried over sodium sulfate, filtered, and concentrated to dryness. The resulting residue is purified by medium pressure liquid chromatography, eluting with ethyl acetate:hexane (1:1). Fractions containing pure product are combined and concentrated to afford 2.5 g (71%) of the title compound. LC-ES/MS m/z 519.2 [M+Na]$^+$, $T_R$=3.77, 3.81 min.

Preparation 18

3-Fluoro-2-methoxy-benzaldehyde

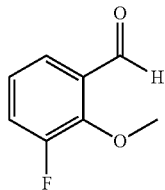

A mixture of 3-fluorosalicylaldehyde (3.52 g, 25.12 mmol) and cesium carbonate (20.46 g, 62.81 mmol) in N,N-dimethylformamide (30 mL) is treated with iodomethane (3.13 mL, 50.2 mmol) and stirred at room temperature under nitrogen for 2 h. The reaction mixture is diluted with diethyl ether (150 mL) and washed with 0.5 M hydrochloric acid (2×150 mL). The organic portion is dried over anhydrous sodium sulfate, filtered, and concentrated to afford 3.42 g (88%) of the title compound as a clear oil. $^1$H NMR (400 MHz, CDCl$_3$) δ 7.59 (d, 1H), 7.32 (dd, 1H), 7.04 (m, 1H), 4.04 (s, 3H).

Preparation 19

(3-Fluoro-2-methoxyphenyl)methanol

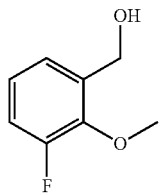

To a solution of 3-fluoro-2-methoxy-benzaldehyde (3.41 g, 22.1 mmol) in methanol (20 mL) is slowly added portionwise sodium borohydride (1.00 g, 26.6 mmol). The reaction is stirred at room temperature under nitrogen overnight. The reaction is diluted with diethyl ether, washed with water twice, dried over anhydrous sodium sulfate, filtered, and concentrated to afford 3.02 g (87%) of the title compound as a clear colorless oil. $^1$H NMR (400 MHz, CDCl$_3$) δ 7.09-6.92 (m, 3H), 4.65 (d, 2H), 3.97 (s, 3H), 2.14 (t, 1H, OH).

Preparation 20

1-(chloromethyl)-3-fluoro-2-methoxybenzene

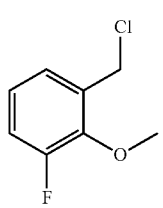

A solution of (3-fluoro-2-methoxyphenyl)methanol (3.02 g, 19.3 mmol) and triethylamine (6.74 mL, 48.4 mmol) in dichloromethane (20 mL) is treated with methanesulfonyl chloride (2.99 mL, 38.7 mmol) slowly at room temperature and stirred under nitrogen for 3 h. The reaction is the diluted with diethyl ether, washed with 0.5 M hydrochloric acid twice, dried over anhydrous sodium sulfate, filtered, and concentrated to afford the title compound as a yellow oil (2.71 g, 80%). $^1$H NMR (400 MHz, CDCl3) δ 7.15-6.93 (m, 3H), 4.61 (s, 2H), 4.00 (s, 3H).

Preparation 21

(S)-7-Cyano-4-(3-fluoro-2-methoxybenzyl)-1,2,3,4-tetrahydrocyclopenta[b]indol-2-ylcarbamic acid isopropyl ester

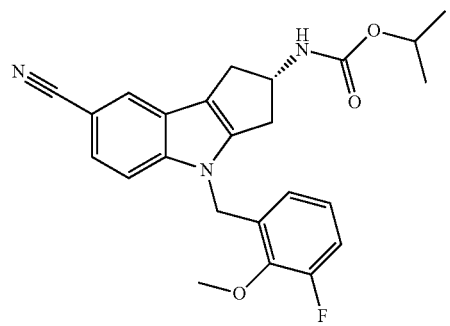 [SMILES: COc1c(F)cccc1Cn1c2c(c3cc(C#N)ccc31)C[C@H](NC(=O)OC(C)C)C2]

A solution of (S)-7-cyano-1,2,3,4-tetrahydrocyclopenta[b]indol-2-ylcarbamic acid isopropyl ester (1.50 g, 5.29 mmol) and 1-(chloromethyl)-3-fluoro-2-methoxybenzene (1.11 g, 6.35 mmol) in N,N-dimethylformamide (10 mL) is treated with cesium carbonate (2.59 g, 7.94 mmol) at room temperature and stirred overnight under nitrogen. The reaction mixture is diluted with water and ether/hexanes. The white solids that crash out of solution are filtered, rinsed with water, ether, hexanes, and dried under vacuum at 50° C. for 48 h to obtain the title compound as a white solid (2.18 g, 98%). LC-ES/MS m/z 422.2 [M+H]$^+$, T$_R$=4.57 min.

Preparation 22

[(S)-7-Cyano-4-(2-methoxy-benzyl)-1,2,3,4-tetrahydro-cyclopenta[b]indol-2-yl]-carbamic acid isopropyl ester

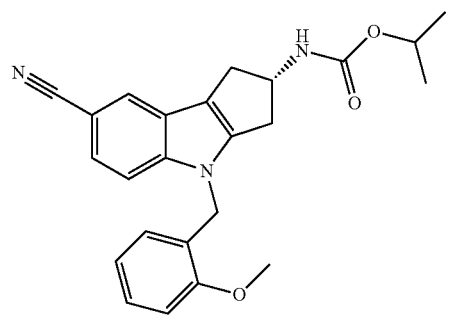 [SMILES: COc1ccccc1Cn1c2c(c3cc(C#N)ccc31)C[C@H](NC(=O)OC(C)C)C2]

A mixture of ((S)-7-cyano-1,2,3,4-tetrahydro-cyclopenta[b]indol-2-yl)-carbamic acid isopropyl ester (2.0 g, 7.06 mmol) and cesium carbonate (3.22 g, 9.88 mmol) in DMF (40 mL) is treated with 2-methoxybenzyl chloride (1.16 g, 7.41 mmol). The reaction is heated at 50° C. for 18 h. The reaction is cooled to room temperature and diluted with water (300 mL). The white solid is collected and washed with water. The solid is dried in a 40° C. vacuum oven. After drying, 2.80 g (98%) product is obtained as a white solid. LC-ES/MS m/z 404 [M+H]$^+$, $T_R$=2.83 min.

Preparation 23 tert-Butyl-(4-fluoro-2-methyl-phenoxy)-dimethyl-silane

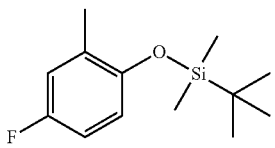 [SMILES: Cc1cc(F)ccc1O[Si](C)(C)C(C)(C)C]

t-Butyldimethylchlorosilane (14.34 g, 93.24 mmol) is combined with 4-fluoro-2-methylphenol (10.00 g, 77.70 mmol) and 1H-imidazole (13.32 g, 194.24 mmol) in dimethylformamide (100 mL) and stirred at room temperature overnight. The reaction is diluted with ether (200 mL) and washed with water (2×100 mL) and brine. The organic portion is dried with sodium sulfate, filtered, and concentrated to afford 18.9 g (100%) of the title compound. GC-ES m/z 240 [M]$^+$, $T_R$=4.06 min.

Preparation 24

(2-Bromomethyl-4-fluoro-phenoxy)-tert-butyl-dimethyl-silane

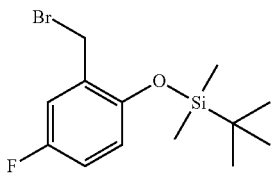 [SMILES: CC(C)(C)[Si](C)(C)Oc1ccc(F)cc1CBr]

A mixture of tert-butyl-(4-fluoro-2-methyl-benzyl)-dimethyl-silane (6.20 g, 25.79 mmol) and N-bromosuccinimide (4.75 g, 26.31 mmol) in carbon tetrachloride (50 mL) is refluxed in a 90° C. oil bath for 10 min and treated with benzoyl peroxide (64 mg, 258 μmol). The resulting suspension is refluxed for 2 h and cooled to room temperature. The solid is removed by filtration and the filtrate concentrated in vacuo. The resulting residue is loaded on a ReadySep® cartridge (25 g) and eluted with hexane (300 mL) to give 6.4 g (78%) of the title compound as a clear oil. GC-ES m/z ($^{79}$Br) 318 [M]$^+$, $T_R$=5.06 min.

Preparation 25

(S)-4-((3-Bromopyridin-4-yl)methyl)-7-cyano-1,2,3,4-tetrahydrocyclopenta[b]indol-2-ylcarbamic acid isopropyl ester

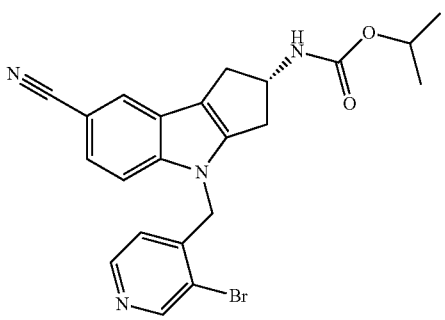 [SMILES: CC(C)OC(=O)N[C@H]1Cc2c(n(Cc3ccncc3Br)c3ccc(C#N)cc23)C1]

A mixture of 3-bromo-4-(chloromethyl)pyridine (3.16 g, 11.5 mmol), ((S)-7-cyano-1,2,3,4-tetrahydro-cyclopenta[b]indol-2-yl)-carbamic acid isopropyl ester (2.50 g, 8.82 mmol) and cesium carbonate (4.31 g, 13.2 mmol) in dimethylformamide (20 mL) is stirred at room temperature under nitrogen overnight. The reaction mixture is then diluted with ethyl acetate, dichloromethane, and water. The organic phase is separated, washed with water twice, dried over anhydrous sodium sulfate, filtered, and concentrated in vacuo to obtain a brown oil (~4.75 g). The oil is triturated with hexanes twice, then with ether twice. It is then purified by flash chromatography eluting with 30 to 60% ethyl acetate/hexanes to obtain an off-white solid (3.23 g, 81%). LC-ES/MS m/z ($^{79}$Br/$^{81}$Br) 453.0/455.0 [M+H]$^+$.

Preparation 26

(S)-4-((4-Chloro-3-methoxypyridin-2-yl)methyl)-7-cyano-1,2,3,4-tetrahydrocyclopenta[b]indol-2-ylcarbamic acid isopropyl ester

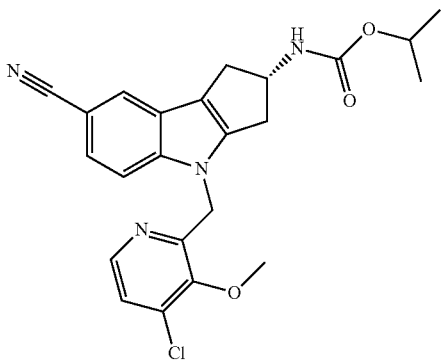 [SMILES: COc1c(Cl)ccnc1Cn1c2c(c3cc(C#N)ccc31)C[C@H](NC(=O)OC(C)C)C2]

To a solution of (S)-isopropyl 7-cyano-1,2,3,4-tetrahydrocyclopenta[b]indol-2-ylcarbamate (680 mg, 2.40 mmol) and 4-chloro-2-(chloromethyl)-3-methoxypyridine (553 mg, 2.88 mmol) in dimethylformamide (5 mL) is added cesium carbonate (1.17 g, 3.60 mmol) and the mixture stirred at room temperature overnight. The reaction mixture is diluted with water and the beige solid is filtered. It is rinsed with water and then dried in a vacuum oven at 50° C. for 48 h to obtain a gray solid (970 mg, 92%). LC-ES/MS m/z 439.0 [M+H]$^+$.

Preparation 27

(S)-4-((3-Methoxypyridin-2-yl)methyl)-7-cyano-1,2,3,4-tetrahydrocyclopenta[b]indol-2-ylcarbamic acid isopropyl ester

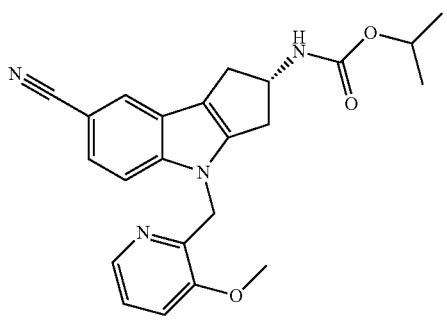 [SMILES: COc1cccnc1Cn1c2c(c3cc(C#N)ccc31)C[C@H](NC(=O)OC(C)C)C2]

A mixture of (S)-isopropyl 4-((4-chloro-3-methoxypyridin-2-yl)methyl)-7-cyano-1,2,3,4-tetrahydrocyclopenta[b]indol-2-ylcarbamate (12.53 g, 28.55 mmol) and 10% palladium on carbon (1.00 g) in methanol (150 mL) is hydrogenated at 50 psi at room temperature overnight. A fresh batch of 10% palladium on carbon (1.2 g) is slurried in water (~2 mL) and added to the reaction mixture, which is hydrogenated (50 psi) at room temperature overnight. The catalyst is filtered off and the solution is concentrated under reduced pressure to obtain a pale yellow solid. The solid is triturated with ether twice and dried under high vacuum to afford a yellow solid (10.80 g, 94%). LC-ES/MS m/z 405.2 [M+H]$^+$

EXAMPLE 1

[(S)-7-Cyano-4-((2R,3S)-3-hydroxy-pyrrolidin-2-ylmethyl)-1,2,3,4-tetrahydrocyclopenta[b]indol-2-yl]-carbamic acid isopropyl ester

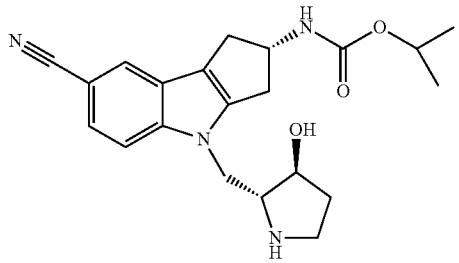 [SMILES: CC(C)OC(=O)N[C@H]1Cc2c(n(C[C@H]3NCC[C@@H]3O)c3ccc(C#N)cc23)C1]

A solution of (2R,3S)-2-((S)-7-cyano-2-isopropoxycarbonylamino-2,3-dihydro-1H-cyclopenta[b]indol-4-ylmethyl)-3-hydroxy-pyrrolidine-1-carboxylic acid tert-butyl ester (0.50 g, 1.04 mmol) in methanol (20 mL) is treated with 4 N hydrogen chloride in 1,4-dioxane (20 mL), stirred at room temperature for 3 h and concentrated. The residue is suspended in ethyl acetate (200 mL) and treated with 2 N aqueous sodium hydroxide solution (20 mL). The organic layer is washed with brine, dried over sodium sulfate, and concentrated. The resulting residue is purified by medium pressure liquid chromatography, eluting with methanol:chloroform (5:95). Fractions containing pure product are combined and concentrated to afford 0.38 g (96%) of the title compound. LC-ES/MS/MS m/z 383.2 [M+H]$^+$, T$_R$=1.86 min.

EXAMPLE 2

[(S)-7-Cyano-4-((2R,3S)-3-hydroxy-1-methyl-pyrrolidin-2-ylmethyl)-1,2,3,4-tetrahydrocyclopenta[b]indol-2-yl]-carbamic acid isopropyl ester

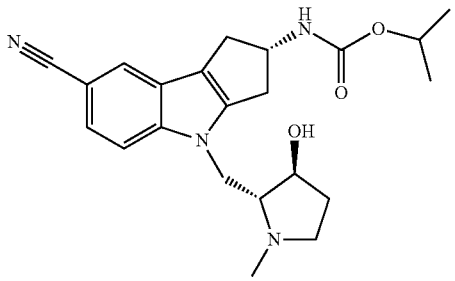 [SMILES: CC(C)OC(=O)N[C@H]1Cc2c(n(C[C@@H]3[C@@H](O)CCN3C)c3ccc(C#N)cc23)C1]

A solution of (2R,3S)-2-((S)-7-cyano-2-isopropoxycarbonylamino-2,3-dihydro-1H-cyclopenta[b]indol-4-ylmethyl)-3-hydroxy-pyrrolidine-1-carboxylic acid tert-butyl ester (3.10 g, 6.42 mmol) in ethanol (20 mL) is treated with 4 N hydrogen chloride in 1,4-dioxane (20 mL) and stirred at room temperature for 3 h. The resulted solution is concentrated in vacuo and suspended in ethyl acetate (200 mL) and treated with 2 N aqueous sodium hydroxide (70 mL). The organic layer is washed with brine, dried over sodium sulfate, and concentrated. The resulting residue is dissolved in chloroform (100 mL) and treated with formaldehyde (1.45 mL, 19.27 mmol) and sodium triacetoxyborohydride (4.25 g, 19.27 mmol). The resulting suspension is stirred overnight at room temperature. The suspension is treated with saturated sodium bicarbonate solution (40 mL) and stirred for 30 min. The resulting suspension is diluted with dichloromethane (100 mL) and washed with water (3×100 mL) and brine. The organic portion is dried over sodium sulfate, filtered, and concentrated to dryness. The resulting residue is purified by medium pressure liquid chromatography, eluting with methanol:chloroform (5:95). Fractions containing pure product are combined and concentrated to afford 1.6 g (63%) of the title compound. LC-ES/MS m/z 397.2 [M+H]$^+$, T$_R$=1.78 min.

EXAMPLE 3

[(S)-7-Cyano-4-((2R,3S)-3-hydroxy-1-ethyl-pyrrolidin-2-ylmethyl)-1,2,3,4-tetrahydro-cyclopenta[b]indol-2-yl]-carbamic acid isopropyl ester

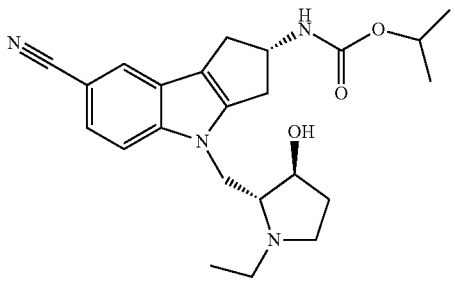 [SMILES: CCN1CC[C@H](O)[C@H]1Cn1c2c(c3cc(C#N)ccc31)C[C@H](NC(=O)OC(C)C)C2]

A solution of [(S)-7-cyano-4-((2R,3S)-3-hydroxy-pyrrolidin-2-ylmethyl)-1,2,3,4-tetrahydro-cyclopenta[b]indol-2-yl]-carbamic acid isopropyl ester (300 mg, 784.4 µmol) in acetonitrile (20 mL) is treated with acetaldehyde (1.0 mL, 17.80 mmol) and sodium triacetoxyborohydride (520 mg, 2.35 mmol) and stirred at room temperature overnight. The suspension is treated with saturated sodium bicarbonate solution (40 mL) and stirred for 30 min. The resulting suspension is diluted with dichloromethane (100 mL) and washed with water (3×100 mL) and brine. The organic portion is dried over sodium sulfate, filtered, and concentrated to dryness. The resulting residue is purified by medium pressure liquid chromatography, eluting with methanol:chloroform (5:95). Fractions containing pure product are combined and concentrated to afford 0.1 g (31%) of the title compound. LC-ES/MS m/z 144.2 [M+H]$^+$, T$_R$=1.94 min.

EXAMPLE 4

[(S)-7-Cyano-4-((2R,3R)-3-hydroxy-1-methyl-pyrrolidin-2-ylmethyl)-1,2,3,4-tetrahydro-cyclopenta[b]indol-2-yl]-carbamic acid isopropyl ester

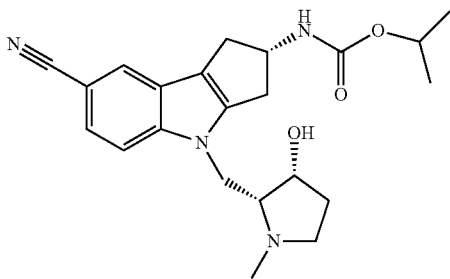 [SMILES: CC(C)OC(=O)N[C@H]1Cc2c(n(C[C@@H]3[C@H](O)CCN3C)c3ccc(C#N)cc23)C1]

A solution of [(S)-7-cyano-4-((2R,3R)-3-hydroxy-pyrrolidin-2-ylmethyl)-1,2,3,4-tetrahydro-cyclopenta[b]indol-2-yl]-carbamic acid isopropyl ester hydrochloride salt (380 mg, 907.1 μmol) in acetonitrile (50 mL) is treated with methanol (5 mL) until most of the solid is dissolved and then treated with formaldehyde (136.3 μL, 1.81 mmol) and sodium triacetoxyborohydride (400.5 mg, 1.81 mmol). The reaction is stirred at room temperature overnight. Saturated aqueous sodium bicarbonate solution (50 mL) is added and stirred for 30 min. The mixture is diluted with ethyl acetate (120 mL) and the resulting suspension is washed with water (3×100 mL) and brine. The organic portion is dried over sodium sulfate, filtered, and concentrated to dryness. The residue is purified by medium pressure liquid chromatography, eluting with methanol:chloroform (5:95). Fractions containing pure product are combined and concentrated to afford 0.2 g (61%) of the title compound. LC-ES/MS m/z 397.2 [M+H]$^+$, T$_R$=1.87 min.

EXAMPLE 5

[(S)-7-Cyano-4-(trans-3-hydroxy-1-methyl-3-methyl-pyrrolidin-2-ylmethyl)-1,2,3,4-tetrahydro-cyclopenta[b]indol-2-yl]-carbamic acid isopropyl ester (racemic)

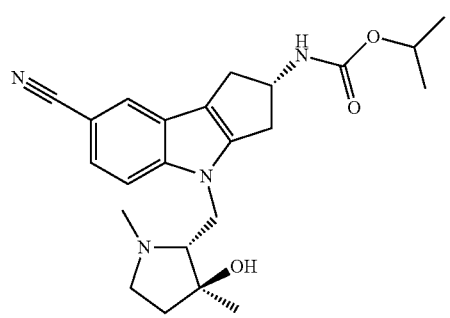

+

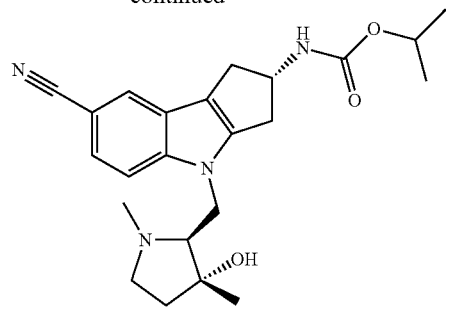

A mixture of trans-2-((S)-7-cyano-2-isopropoxycarbonylamino-2,3-dihydro-1H-cyclopenta[b]indol-4-ylmethyl)-3-hydroxy-3-methyl-pyrrolidine-1-carboxylic acid tert-butyl ester (2.50 g, 5.03 mmol) in 1,4-dioxane (15 mL) and methanol (2 mL) is treated with 4 N hydrogen chloride in 1,4-dioxane (15 mL) and stirred at room temperature for 3 h. The reaction becomes a white solid suspension with a reddish solution. The suspension is concentrated and the residue is suspended in acetonitrile (30 mL) and treated with 30% formaldehyde aqueous solution (1.13 mL, 15.10 mmol) and sodium triacetoxyborohydride (3.33 g, 15.10 mmol). The resulting suspension is stirred overnight. Treat the suspension with saturated aqueous sodium bicarbonate and stir for 30 min. Dilute the suspension with ethyl acetate (120 mL) and wash it with water (3×100 mL) and brine. Dry the organic portion over sodium sulfate, filter, and concentrate to dryness. Purify the residue by medium pressure liquid chromatography, eluting with ethyl acetate:hexane (1:1). Fractions containing pure product are combined and concentrated to afford 1.75 g (84%) of the title compound. LC-ES/MS m/z 411.2 [M+H]$^+$, T$_R$=1.96 min.

EXAMPLE 6 & 7

Isomer 1 & Isomer 2 of [(S)-7-Cyano-4-(trans-3-hydroxy-1-methyl-3-methyl-pyrrolidin-2-ylmethyl)-1,2,3,4-tetrahydro-cyclopenta[b]indol-2-yl]-carbamic acid isopropyl ester

[(S)-7-Cyano-4-(trans-3-hydroxy-1-methyl-3-methyl-pyrrolidin-2-ylmethyl)-1,2,3,4-tetrahydro-cyclopenta[b]indol-2-yl]-carbamic acid isopropyl ester (racemic) (2.15 g, 5.24 mmol) is separated with chiralpak® AD-H, 4.6×150 mm column, eluting 1 mL/min with acetonitrile:methanol:dimethylethylamine (30:70:0.2), detecting at 225 nm. Collect peak #1 from 2.0 minute to 2.5 minute and peak #2 from 4.0 minute to 7.0 minute. Fractions containing pure product are combined and concentrated to afford 0.926 g (43%) of Isomer 1 and 0.822 g (38%) of Isomer 2.

EXAMPLE 8

[(S)-7-cyano-4-(3-fluoro-2-hydroxybenzyl)-1,2,3,4-tetrahydrocyclopenta[b]indol-2-y]-carbamic acid isopropyl ester

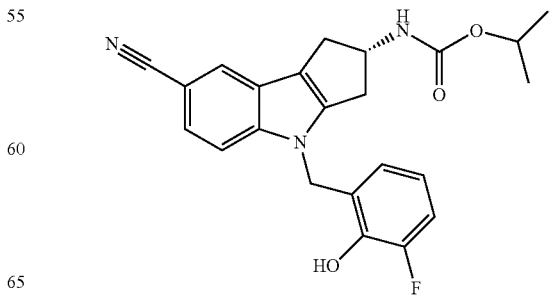

To a solution of (S)-isopropyl 7-cyano-4-(3-fluoro-2-methoxybenzyl)-1,2,3,4-tetrahydrocyclopenta[b]indol-2-yl-carbamate (1.88 g, 4.46 mmol) in dichloromethane (50 mL) is added 1 M boron tribromide in dichloromethane (13.4 mL, 13 4 mmol) at 0° C. and stirred overnight. The reaction is quenched with slightly wet acetonitrile. The volatiles are removed under reduced pressure and the residue is dried under high vacuum. It is then purified by column chromatography with 5% ethyl acetate in chloroform to obtain a yellow solid. The solid is suspended in a minimum amount of dichloromethane and allowed to sit at room temperature. White solids crash out. They are filtered and briefly rinsed with dichloromethane. The mother liquor is concentrated and the procedure is repeated with the residue three times. The white solids are combined to afford the title compound (1.17 g, 64%). LC-ES m/z 408.2 [M+H]$^+$, T$_R$=4.08 min.

EXAMPLE 9

[(S)-7-Cyano-4-(2-hydroxy-benzyl)-1,2,3,4-tetrahydro-cyclopenta[b]indol-2-yl]-carbamic acid isopropyl ester

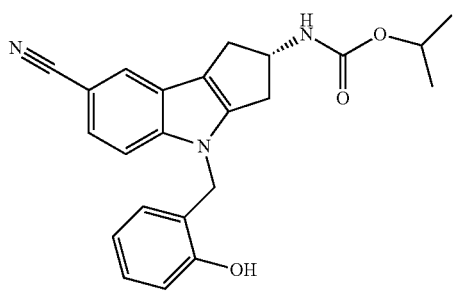 [SMILES: CC(C)OC(=O)N[C@H]1Cc2c(n(Cc3ccccc3O)c3ccc(C#N)cc23)C1]

To a 0° C. solution of [(S)-7-cyano-4-(2-methoxy-benzyl)-1,2,3,4-tetrahydro-cyclopenta[b]indol-2-yl]-carbamic acid isopropyl ester (1.50 g, 3.72 mmol) in dichloromethane (37 mL) is added BBr$_3$ (1.0 M in dichloromethane, 11.2 mL, 11.2 mmol). The reaction is allowed to warm up to room temperature and stirred for 18 h. The reaction is quenched with saturated aqueous NH$_4$Cl. Water (70 mL) is added and the crude product is extracted with dichloromethane (75 mL) and EtOAc (2×75 mL). The combined organics are dried over Na$_2$SO$_4$, filtered, and concentrated. The crude product is purified on silica gel (40 g, 30% EtOAc/hexanes) and then re-purified on silica gel (40 g, 5% acetonitrile/dichloromethane) to give 1.00 g of product that is about 90% pure.

The reaction is repeated on 1.77 g (4.38 mmol) and worked up in the same fashion. The crude product is combined with the 90% pure product from the previous run, and the combined product is purified on silica gel (240 g, 2:33:65 MeOH/dichloromethane/hexanes) to give 991 mg (37% combined yield for the two reactions) of the title compound as a white solid. $^1$H-NMR (400 MHz, CDCl$_3$) δ 7.70 (s, 1H), 7.33 (d, J=8.8 Hz, 1H), 7.27-7.23 (m, 1H), 7.12-7.08 (m, 1H), 6.79-6.71 (m, 3H), 6.14-6.11 (m, 1H), 5.19 (s, 2H), 5.05-4.97 (m, 1H), 4.93-4.80 (m, 2H), 3.30-3.23 (m, 2H), 2.69-2.62 (m, 2H), 1.21 (t, J=5.9 Hz, 6H).

EXAMPLE 10

[(S)-7-Cyano-4-(5-fluoro-2-hydroxy-benzyl)-1,2,3,4-tetrahydro-cyclopenta[b]indol-2-yl]carbamic acid isopropyl ester

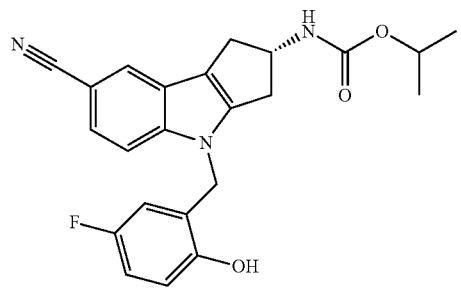 [SMILES: CC(C)OC(=O)N[C@H]1Cc2c(n(Cc3cc(F)ccc3O)c3ccc(C#N)cc23)C1]

A mixture of ((S)-7-cyano-1,2,3,4-tetrahydro-cyclopenta[b]indol-2-yl)-carbamic acid isopropyl ester (1.15 g, 4.06 mmol) and cesium carbonate (1.60 g, 4.87 mmol) in dimethylformamide (15 mL) is stirred at −40° C. (dry ice bath) for 30 min and treated with (2-bromomethyl-4-fluoro-phenoxy)-tert-butyl-dimethyl-silane (1.56 g, 4.87 mmol). The reaction is stirred at −40° C. (dry ice bath) for 5 h and warmed up to room temperature for 6 h. The resulting suspension is diluted with ethyl acetate (120 mL) and washed with water (3×100 mL) and brine. The organic portion is dried over sodium sulfate, filtered, and concentrated to dryness. The resulting residue is purified by medium pressure liquid chromatography, eluting with ethyl acetate:hexane (1:1). Fractions containing pure product are combined and concentrated to afford 0.6 g of the silyl protected material. Dissolve it in tetrahydrofuran (10 mL) and add tetrabutylammonium fluoride solution (1 M, 5 mL) at room temperature. Stir the mixture for one hour and concentrate. The residue is diluted with ethyl acetate (100 mL) and washed with water and brine. The organic portion is dried over sodium sulfate, and concentrated. The resulting residue is purified by medium pressure liquid chromatography, eluting with acetonitrile:dichloromethane (8:92). Fractions containing pure product are combined and concentrated. A white solid is obtained and recrystallized with acetonitrile to give 0.35 g (21%) of the title compound. LC-ES m/z 408.2 [M+H]$^+$, T$_R$=4.09 min.

EXAMPLE 11

(S)-7-Cyano-4-((3-hydroxypyridin-4-yl)methyl)-1,2,3,4-tetrahydrocyclopenta[b]indol-2-ylcarbamic acid isopropyl ester

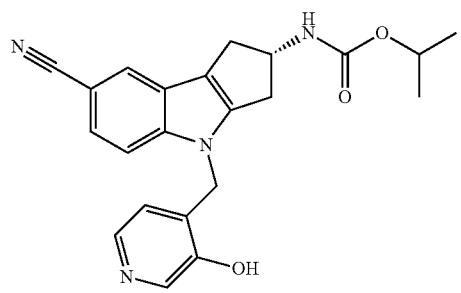

A mixture of (S)-4-((3-bromopyridin-4-yl)methyl)-7-cyano-1,2,3,4-tetrahydrocyclopenta[b]indol-2-ylcarbamic acid isopropyl ester (3.81 g, 7.05 mmol), potassium hydroxide (1.34 g, 23.9 mmol), 2-di-tert-butylphosphino-3,4,5,6-tetramethyl-2',4',6'-triisopropyl-1,1'-biphenyl (230 mg, 479 μmol), tris(dibenzylideneacetone)dipalladium (110 mg, 120 μmol) in water (50 mL) and 1,4-dioxane (50 mL) is heated at 100° C. for one hour. Tris(dibenzylideneacetone)dipalladium (110 mg, 120 μmol) and 2-di-tert-butylphosphino-3,4,5,6-tetramethyl-2',4',6'-triisopropyl-1,1'-biphenyl (230 mg, 479 μmol) are added and the mixture is heated for 3 h. The reaction is diluted with water and dichloromethane. The layers are then separated and the aqueous layer is washed with dichloromethane twice. The aqueous portion is acidified to pH 1-2 with a few drops of 5 M HCl and then neutralized to pH 7 with potassium carbonate. Ethyl acetate is added and the bi-layer is filtered. The organic phase is separated, dried over anhydrous sodium sulfate, filtered, and concentrated in vacuo to obtain a brown residue. The residue is triturated with ether twice and dried under vacuum. It is then purified by flash chromatography eluting with 1% to 6% methanol in chloroform to obtain impure product (~2.8 g). It is purified by preparative super critical fluid chromatography (column: ethylpyridine 20×150 mm (Princeton Chromatography, Inc.); flow rate: 70 mL/min @ 35° C. and 100 psi; eluent: 5-50% MeOH with 0.1% isopropylamine:carbon dioxide) to obtain the title compound as a white solid (548 mg, 20%). LC-ES/MS m/z 391.2 [M+H]$^+$, $T_R$=2.63 min.

EXAMPLE 12

(S)-7-Cyano-4-((3-hydroxypyridin-2-yl)methyl)-1,2,3,4-tetrahydrocyclopenta[b]indol-2-ylcarbamic acid isopropyl ester

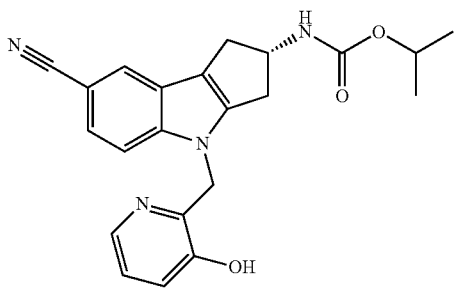 [SMILES: CC(C)OC(=O)N[C@H]1Cc2c(n(Cc3ncccc3O)c3ccc(C#N)cc23)C1]

(S)-4-((3-Methoxypyridin-2-yl)methyl)-7-cyano-1,2,3,4-tetrahydrocyclopenta[b]indol-2-ylcarbamic acid isopropyl ester (4.59 g, 11.4 mmol) and pyridine hydrochloride (21.0 g, 182 mmol) are mixed with a magnetic stirrer in a 75 mL sealed vessel that is immersed in a preheated oil bath (170° C.). The solids melt within approximately 30 sec and are stirred for 60 min. The mixture is cooled to room temperature, transferred to another flask, and dissolved in tetrahydrofuran (100 mL) and water (100 mL). Potassium carbonate (40 g) is added slowly in portions and after stirring for 5 min a 1 M solution of isopropyl chloroformate in toluene (34.0 mL, 34.0 mmol) is added at room temperature. A portion of the solvent is removed under reduced pressure and the residue is diluted with dichloromethane and ethyl acetate. The brown insoluble residue is filtered off and the phases are separated. The organic phase is washed with 10% potassium carbonate once, dried over anhydrous sodium sulfate, filtered, and concentrated in vacuo to obtain a brown foam. The foam is dissolved in methanol (20 mL), 2 M sodium hydroxide (10 mL) is added and the reaction is stirred at room temperature for 1 hour. The solvent is removed under reduced pressure. The residue is dissolved in 0.5 M HCl/EtOAc/CHCl$_3$ and the bilayer is filtered. It is then acidified to pH 7-8 with 5% potassium carbonate. The phases are separated and the organic phase is washed with 5% potassium carbonate once, dried over anhydrous sodium sulfate, filtered, and concentrated in vacuo to obtain an orange foam. The foam is purified by silica flash chromatography eluting with 10 to 40% ethyl acetate/chloroform to obtain a red solid (3.33 g). The solid is dissolved in 0.5 M sodium hydroxide (30 mL). The aqueous layer is washed with dichloromethane twice and the organic layers are discarded. The aqueous layer is adjusted to pH 4-5 with 5 M hydrochloric acid. An off-white/yellow solid crashes out of solution. The pH is adjusted to 8-9 with potassium carbonate, the yellow solid is collected by filtration and air dried for one hour. It is then suspended in a minimum amount of acetonitrile, filtered, and rinsed with a minimum amount of acetonitrile. The mother liquor is concentrated and the procedure is repeated two times to afford a white powder, which is dried under high vacuum overnight to obtain the title compound as a white solid (1.45 g, 33%). LC-ES/MS m/z 391.2 [M+H]$^+$, $T_R$=3.32 min.

ALTERNATE SYNTHESIS TO EXAMPLE 12

Preparation 27

(3-Allyloxy-pyridin-2-yl)-methanol

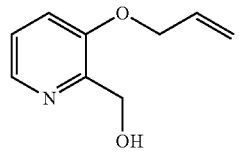

Hydroxy-2-(hydroxymethyl)pyridine hydrochloride (50 g, 339.6 mmol) and methanol (250 mL) are combined under nitrogen and cooled to 22° C. To the vigorously stirred mixture is added 4.5 M sodium methoxide in MeOH (170.8 mL, 747.2 mmol). The mixture is stirred at room temperature for 2 h and then the solvent is evaporated. The resulting material is dissolved in DMSO (250 mL), allyl bromide (41 g, 339.6 mmoles) is added, and the mixture stirred for 18 h at room temperature. The reaction mixture is added to water (800 mL) and extracted with methylene chloride (3×80 mL). The organic portions are combined and dried over sodium sulfate, filtered, and the solvent evaporated to afford the title compound (34.4 g, 62%). LC-ES/MS m/z 166.1 [M+H]$^+$.

Preparation 28

3-Allyloxy-2-chloromethyl-pyridine

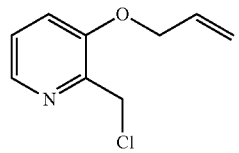

(3-Allyloxy-pyridin-2-yl)-methanol (34 g, 205.8 mmol) is dissolved in dichloromethane (340 mL) under nitrogen and triethylamine (34.4 mL, 247 mmol) is added at 22° C. The mixture is warmed to room temperature in a water bath and methanesulfonyl chloride (16.7 mL, 216 mmol) is added keeping the temperature below 30° C. The reaction is allowed to stir overnight at room temperature. Water (500 mL is added and the mixture stirred for 10 min. The organic portion is separated and washed with a solution of saturated NaHCO$_3$ (100 mL). The organic portion is dried over sodium sulfate, filtered, and the solvent evaporated. The resulting residue is dried under vacuum to constant weight to afford the title compound (29 g, 79%). LC-ES/MS m/z: 184.6 [M+H]$^+$.

Preparation 29

[(S)-4-(3-Allyloxy-pyridin-2-ylmethyl)-7-cyano-1,2, 3,4-tetrahydro-cyclopenta[b]indol-2-yl]-carbamic acid isopropyl ester

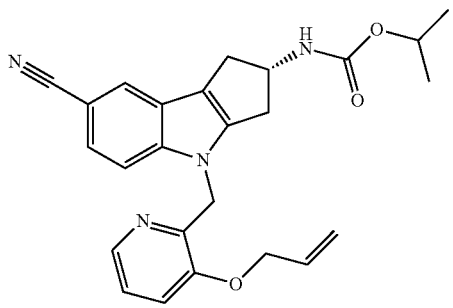 [SMILES: C=CCOc1cccnc1Cn1c2c(c3cc(C#N)ccc31)C[C@H](NC(=O)OC(C)C)C2]

((S)-7-Cyano-1,2,3,4-tetrahydro-cyclopenta[b]indol-2-yl)-carbamic acid isopropyl ester (25 g, 88.2 mmol) is dissolved in dimethylformamide (150 mL) under nitrogen. Cesium carbonate (57.5 g, 176.5 mmol) and 3-allyloxy-2-chloromethyl-pyridine (16.2 g, 88.2 mmol) are added sequentially. The reaction mixture is stirred at 40° C. for 16 h. The reaction is cooled to room temperature and added to water (1250 mL). After one hour of stirring a pale cream solid is filtered. The crude material is purified by recrystallization from i-PrOH and then dried under vacuum to constant weight to afford the title compound (32 g; 84%). LC-ES/MS m/z: 431.2 [M+H]$^+$.

EXAMPLE 12A

[(S)-7-cyano-4-(3-hydroxy-pyridin-2-ylmethyl)-1,2, 3,4-tetrahydro-cyclopenta[b]indol-2-yl]-carbamic acid isopropyl ester

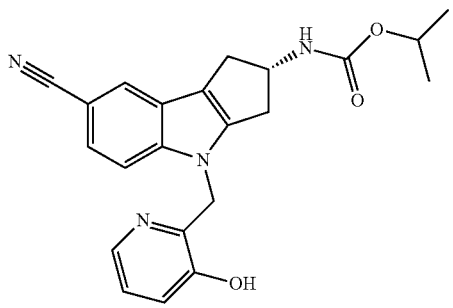 [SMILES: CC(C)OC(=O)N[C@H]1Cc2c(n(Cc3ncccc3O)c3ccc(C#N)cc23)C1]

[(S)-4-(3-Allyloxy-pyridin-2-ylmethyl)-7-cyano-1,2,3,4-tetrahydro-cyclopenta[b]indol-2-yl]-carbamic acid isopropyl ester (40 g, 87.3 mmol) and 1,4-dioxane (400 mL) are combined and the mixture degassed by bubbling in nitrogen for one hour. Then triethylamine (24.4 mL, 174.7 mmol) and formic acid (6.60 mL, 174.7) are added and the mixture heated under nitrogen at 80° C. Tetrakis(triphenylphosphine) palladium (1.02 g, 0.87 mmol) is added while maintaining the nitrogen atmosphere. The reaction is heated at 80° C. for 3 h and then cooled to room temperature. The reaction is filtered through a pad of diatomaceous earth. The filtrate is evaporated and the crude material dried under vacuum to afford a brown solid. The solid is dissolved in NMP (100 mL) and then added to water (1.2 L). A pale cream solid is collected by filtration and dried overnight under vacuum to afford 41 g of crude material. The material is purified by recrystallization from acetonitrile and then dried under vacuum to constant weight to afford the title compound (29.5 g, 86%). LC-ES/MS m/z: 391.1 [M+H]$^+$.

We claim:
1. A compound of Formula (I):

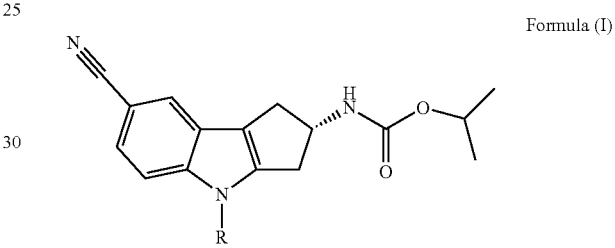

Formula (I)

wherein,

R represents a substitutent selected from the group consisting of

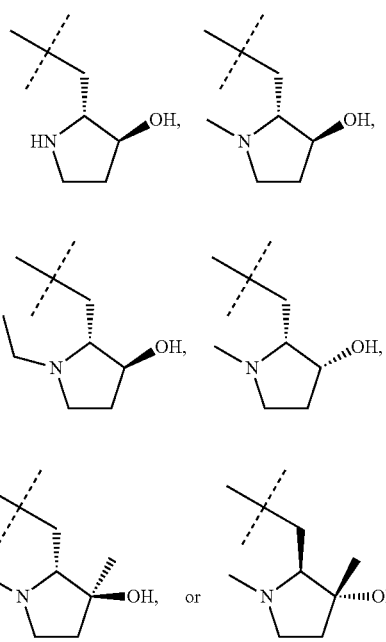

or a pharmaceutically acceptable salt thereof.

2. The compound or salt according to claim 1 wherein R represents

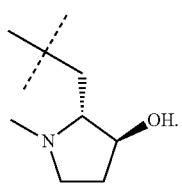

3. A pharmaceutical composition comprising a compound or salt according to claim 1 in combination with one or more pharmaceutically acceptable carriers, diluents, or excipients.

4. A compound of Formula (I),

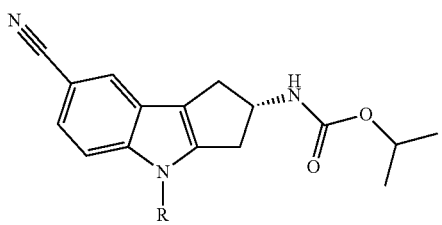

Formula (I)

wherein R represents a substituent selected from the group consisting of

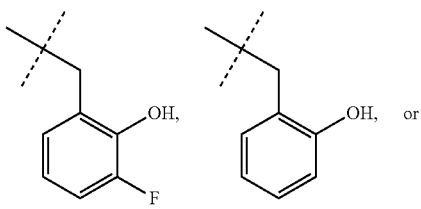

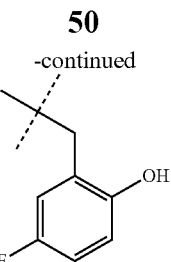

or a pharmaceutical acceptable salt thereof.

5. A pharmaceutical composition comprising a compound or salt according to claim 4, in combination with one or more pharmaceutically acceptable carriers, diluents or excipients.

6. A method of treating reduced bone mass or density, osteoporosis, osteopenia, reduced muscle mass or strength, or erectile dysfunction, comprising administering to a patient in need thereof a compound or salt according to claim 1.

7. The method according to claim 6, for treating reduced bone mass or density, osteoporosis, osteopenia, reduced muscle mass or strength induced by immobilization, disuse or trauma, or erectile dysfunction.

8. The method according to claim 7 for treating erectile dysfunction.

9. The method according to claim 8 further comprising administering to said patient a compound selected from the group consisting of tadalafil, sildenafil citrate and vardenafil hydrochloride.

10. A method of treating reduced bone mass or density, osteoporosis, osteopenia, reduced muscle mass or strength, or erectile dysfunction, comprising administering to a patient in need thereof a compound or salt according to claim 4.

11. The method according to claim 10 for treating reduced bone mass or density, osteoporosis, osteopenia, reduced muscle mass or strength induced by immobilization, disuse or trauma, or erectile dysfunction.

12. The method according to claim 11 for treating erectile dysfunction.

13. The method according to claim 12 further comprising administering to said patient a compound selected from the group consisting of tadalafil, sildenafil citrate and vardenafil hydrochloride.

* * * * *